United States Patent
Beilinson et al.

(10) Patent No.: US 11,807,848 B2
(45) Date of Patent: *Nov. 7, 2023

(54) HIGH THROUGHPUT DISCOVERY OF NEW GENES FROM COMPLEX MIXTURES OF ENVIRONMENTAL MICROBES

(71) Applicant: AGBIOME, INC., Durham, NC (US)

(72) Inventors: Vadim Beilinson, Durham, NC (US); Janice Jones, Apex, NC (US); Jessica Parks, Raleigh, NC (US); Rebecca E. Thayer, Morrisville, NC (US); Daniel J. Tomso, Bahama, NC (US); Scott Joseph Uknes, Apex, NC (US); Sandy Volrath, Durham, NC (US); Eric Russell Ward, Durham, NC (US)

(73) Assignee: AgBiome, Inc., Durham, NC (US)

( * ) Notice: Subject to any disclaimer, the term of this patent is extended or adjusted under 35 U.S.C. 154(b) by 334 days.

This patent is subject to a terminal disclaimer.

(21) Appl. No.: 17/148,210

(22) Filed: Jan. 13, 2021

(65) Prior Publication Data

US 2021/0130811 A1 May 6, 2021

Related U.S. Application Data

(63) Continuation of application No. 15/862,184, filed on Jan. 4, 2018, now Pat. No. 10,920,218, which is a continuation of application No. 14/592,473, filed on Jan. 8, 2015, now Pat. No. 9,896,686.

(60) Provisional application No. 61/925,422, filed on Jan. 9, 2014.

(51) Int. Cl.
| | |
|---|---|
| *C12Q 1/6869* | (2018.01) |
| *C12Q 1/6806* | (2018.01) |
| *C12Q 1/6827* | (2018.01) |
| *C12N 15/10* | (2006.01) |

(52) U.S. Cl.
CPC ....... *C12N 15/1065* (2013.01); *C12Q 1/6806* (2013.01); *C12Q 1/6827* (2013.01); *C12Q 1/6869* (2013.01)

(58) Field of Classification Search
CPC ... C12Q 1/6806; C12Q 1/6827; C12Q 1/6869
See application file for complete search history.

(56) References Cited

U.S. PATENT DOCUMENTS

| | | |
|---|---|---|
| 2010/0029498 A1 | 2/2010 | Gnirke et al. |
| 2011/0154535 A1 | 6/2011 | Abad et al. |
| 2013/0230857 A1 | 9/2013 | Gnirke et al. |
| 2014/0031240 A1 | 1/2014 | Behlke et al. |

FOREIGN PATENT DOCUMENTS

| | | |
|---|---|---|
| WO | WO 2013/014432 | 1/2013 |

OTHER PUBLICATIONS

Cosart et al. BMC Genomics. 2011. 12:347. (Year: 2011).*
Li et al. BioTechniques. 2013. 54(6):321. (Year: 2013).*
Boekhorst et al. BMC Bioinformatics. 2007. 8:356. (Year: 2007).*
Saintenac et al. Genome Biology. 2011. 12:R88 (Year: 2011).*
Terracciano et al. "Hybridization-Based Enrichment and Next Generation Sequencing to Explore Genetic Diversity in Plants". Dynamics of Mathematical Models in Biology. 2016. (Year: 2016).*
Bi et al., "Transcriptome-based exon capture enables highly cost-effective comparative genomic data collection at moderate evolutionary scales," BMC Genomics, 2012, 13:403, pp. 1-14.
Illumina, "SureSelect XT Target Enrichment System for Illumina Paired-End Sequencing Library," Rights in Commercial Computer Software or Computer Software Documentation, Sep. 1, 2012, pp. 1-72.
Janssen et al., "Improved Culturability of Soil Bacteria and Isolation in Pure Culture of Novel Members of the Divisions *Acidobacteria, Actinobacteria, Proteobacteria*, and *Verrucomicrobia*," Applied and Environmental Microbiology, May 2002, 68(5):2391-2396.
Jones et al., "Rapid genetic diagnosis of heritable platelet function disorders with next-generation sequencing: proof-of-principle with Hermansky-Pudlak syndrome," J of Thrombosis and Haemostasis, Feb. 2, 2012, 10(2):306-309.
International Search Report dated Apr. 17, 2015, in PCT/US2015/010648.

* cited by examiner

*Primary Examiner* — Joseph G. Dauner
(74) *Attorney, Agent, or Firm* — Womble Bond Dickinson (US) LLP

(57) ABSTRACT

Compositions and methods for isolating new variants of known gene sequences are provided. The methods find use in identifying variants, particularly homologs, in complex mixtures. Compositions comprise hybridization baits that hybridize to gene families of interest, particularly agricultural interest, in order to selectively enrich the polynucleotides of interest from complex mixtures. Bait sequences may be specific for a number of genes from distinct gene families of interest and may be designed to cover each gene of interest by at least 2-fold. Thus methods disclosed herein are drawn to an oligonucleotide hybridization gene capture approach for identification of new genes of interest from environmental samples. This approach bypasses the need for labor-intensive microbial strain isolation, permits simultaneous discovery of genes from multiple gene families of interest, and increases the potential to discover genes from low-abundance and unculturable organisms present in complex mixtures of environmental microbes.

23 Claims, No Drawings
Specification includes a Sequence Listing.

SEQUENCE LISTING

<160> NUMBER OF SEQ ID NOS: 22

<210> SEQ ID NO 1
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 1
atggataaca atccgaacat caatgaatgc attccttata attgtttaag taaccctgaa      60
gtagaagtat taggtggaga aagaatagaa actggttaca ccccaatcga tatttccttg     120

<210> SEQ ID NO 2
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 2
gtagaagtat taggtggaga aagaatagaa actggttaca ccccaatcga tatttccttg      60
tcgctaacgc aatttctttt gagtgaattt gttcccggtg ctggatttgt gttaggacta     120

<210> SEQ ID NO 3
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 3
tcgctaacgc aatttctttt gagtgaattt gttcccggtg ctggatttgt gttaggacta      60
gttgatataa tatggggaat ttttggtccc tctcaatggg acgcatttcc tgtacaaatt     120

<210> SEQ ID NO 4
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 4
gttgatataa tatggggaat ttttggtccc tctcaatggg acgcatttcc tgtacaaatt    60
gaacagttaa ttaaccaaag aatagaagaa ttcgctagga accaagccat ttctagatta   120

<210> SEQ ID NO 5
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 5
gaacagttaa ttaaccaaag aatagaagaa ttcgctagga accaagccat ttctagatta    60
gaaggactaa gcaatcttta tcaaatttac gcagaatctt ttagagagtg ggaagcagat   120

<210> SEQ ID NO 6
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 6
gaaggactaa gcaatcttta tcaaatttac gcagaatctt ttagagagtg ggaagcagat    60
cctactaatc cagcattaag agaagagatg cgtattcaat tcaatgacat gaacagtgcc   120

<210> SEQ ID NO 7
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 7
cctactaatc cagcattaag agaagagatg cgtattcaat tcaatgacat gaacagtgcc    60
cttacaaccg ctattcctct tttggcagtt caaaattatc aagttcctct tttatcagta   120

<210> SEQ ID NO 8
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 8
cttacaaccg ctattcctct tttggcagtt caaaattatc aagttcctct tttatcagta    60
tatgttcaag ctgcaaattt acatttatca gttttgagag atgtttcagt gtttggacaa   120

<210> SEQ ID NO 9
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 9
tatgttcaag ctgcaaattt acatttatca gttttgagag atgtttcagt gtttggacaa    60
aggtggggat tgatgccgc gactatcaat agtcgttata atgatttaac taggcttatt   120

<210> SEQ ID NO 10

```
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 10
aggtggggat tgatgccgc gactatcaat agtcgttata atgatttaac taggcttatt      60
ggcaactata cagattatgc tgtgcgctgg tacaatacgg gattagagcg tgtatgggga    120

<210> SEQ ID NO 11
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 11
ggcaactata cagattatgc tgtgcgctgg tacaatacgg gattagagcg tgtatgggga     60
ccggattcta gagattgggt aaggtataat caatttagaa gagagctaac acttactgta   120

<210> SEQ ID NO 12
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 12
ccggattcta gagattgggt aaggtataat caatttagaa gagagctaac acttactgta     60
ttagatatcg ttgctctatt ctcaaattat gatagtcgaa ggtatccaat tcgaacagtt   120

<210> SEQ ID NO 13
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 13
ttagatatcg ttgctctatt ctcaaattat gatagtcgaa ggtatccaat tcgaacagtt     60
tcccaattaa caagagaaat ttatacgaac ccagtattag aaaatttga tggtagtttt    120

<210> SEQ ID NO 14
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 14
tcccaattaa caagagaaat ttatacgaac ccagtattag aaaatttga tggtagtttt     60 cgtggaatgg ctcagagaat agaacagaat attaggcaac cacatcttat ggatatcctt  120

<210> SEQ ID NO 15
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 15
cgtggaatgg ctcagagaat agaacagaat attaggcaac cacatcttat ggatatcctt    60
```
aatagtataa ccatttatac tgatgtgcat agaggcttta attattggtc agggcatcaa    120

<210> SEQ ID NO 16
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 16
aatagtataa ccatttatac tgatgtgcat agaggcttta attattggtc agggcatcaa    60
ataacagctt ctcctgtagg gttttcagga ccagaattcg cattccctttt atttgggaat    120

<210> SEQ ID NO 17
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 17
ataacagctt ctcctgtagg gttttcagga ccagaattcg cattccctttt atttgggaat    60 gcggggaatg cagctccacc cgtacttgtc tcattaactg gtttggggat ttttagaaca    120

<210> SEQ ID NO 18
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 18
gcggggaatg cagctccacc cgtacttgtc tcattaactg gtttggggat ttttagaaca    60
ttatcttcac ctttatatag aagaattata cttggttcag cccaaataa tcaggaactg    120

<210> SEQ ID NO 19
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 19
ttatcttcac ctttatatag aagaattata cttggttcag cccaaataa tcaggaactg    60 tttgtccttg atggaacgga gttttctttt gcctccctaa cgaccaactt gccttccact    120

<210> SEQ ID NO 20
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 20
tttgtccttg atggaacgga gttttctttt gcctccctaa cgaccaactt gccttccact    60
atatatagac aaagggtac agtcgattca ctagatgtaa taccgccaca ggataatagt    120

<210> SEQ ID NO 21
<211> LENGTH: 120
<212> TYPE: DNA
<213> ORGANISM: Artificial Sequence
<220> FEATURE:

-continued

```
<223> OTHER INFORMATION: Synthethic Sequence

<400> SEQUENCE: 21
atatatagac aaaggggtac agtcgattca ctagatgtaa taccgccaca ggataatagt        60
gtaccacctc gtgcgggatt tagccatcga ttgagtcatg ttacaatgct gagccaagca       120

<210> SEQ ID NO 22
<211> LENGTH: 120
<212> TYPE: DNA
<213> ORGANISM: Artificial Sequence
<220> FEATURE:
<223> OTHER INFORMATION: Synthethic Sequence

<400> SEQUENCE: 22
gtaccacctc gtgcgggatt tagccatcga ttgagtcatg ttacaatgct gagccaagca        60
gctggagcag tttacacctt gagagctcca acgttttctt ggcagcatcg cagtgctgaa       120
```

HIGH THROUGHPUT DISCOVERY OF NEW GENES FROM COMPLEX MIXTURES OF ENVIRONMENTAL MICROBES

CROSS-REFERENCE TO RELATED APPLICATIONS

This application is a continuation of U.S. application Ser. No. 15/862,184, filed Jan. 4, 2018, which is a continuation of U.S. application Ser. No. 14/592,473, filed Jan. 8, 2015, and claims the benefit of and priority under 35 U.S.C. § 119(e) to U.S. Provisional Application Ser. No. 61/925,422, filed Jan. 9, 2014, the disclosures of each application are herein incorporated by reference in their entirety.

REFERENCE TO "SEQUENCE LISTING" SUBMITTED AS AN ASCII TEXT FILE VIA EFS-WEB

The Sequence Listing written in file 13689515_1.txt, created on Jan. 3, 2018, 6,041 bytes, machine format IBM-PC, MS-Windows operating system, in full accordance with 37 C.F.R. §§ 1.821-1.825, is hereby incorporated by reference in its entirety for all purposes.

FIELD

The invention is drawn to high throughput methods of gene discovery.

BACKGROUND

Given their diversity and abundance, microbial genomes represent an expansive untapped source for new gene discovery. Despite a relative lack of exploration, several gene families of agricultural and biomedical interest have been discovered in microbes and include genes that confer resistance to herbicides and pests in plants, as well as genes for antibiotic biosynthesis and antibiotic resistance. Current methods for new gene discovery from microbial genomes rely on screening isolated strains for activity in a bioassay and characterization of genes of interest by sequencing. However, complex samples containing mixed cultures of organisms often contain species that cannot be cultured or are difficult to perform traditional methods of gene discovery. Thus, a high throughput method of new gene identification where up to millions of culturable and non-culturable microbes can be queried simultaneously would be advantageous for identifying new genes or improved variants of known genes.

SUMMARY

Compositions and methods for isolating new variants of known gene sequences are provided. The methods find use in identifying variants, particularly homologs in complex mixtures. Compositions comprise hybridization baits that hybridize to gene families of interest, particularly agricultural interest, in order to selectively enrich the polynucleotides of interest from complex mixtures. Bait sequences may be specific for a number of genes from distinct gene families of interest and may be designed to cover each gene of interest by at least 2-fold. Thus methods disclosed herein are drawn to an oligonucleotide hybridization gene capture approach for identification of new genes of interest from environmental samples. This approach bypasses the need for labor-intensive microbial strain isolation, permits simultaneous discovery of genes from multiple gene families of interest, and increases the potential to discover genes from low-abundance and unculturable organisms present in complex mixtures of environmental microbes.

DETAILED DESCRIPTION

Methods for identifying variants of known gene sequences from complex mixtures are provided. The methods use labeled hybridization baits or bait sequences that correspond to a portion of known gene sequences to capture similar sequences from complex environmental samples. Once the DNA sequence is captured, subsequent sequencing and analysis can identify variants of the known gene sequences in a high throughput manner.

The methods of the invention are capable of identifying and isolating gene sequences, and variants thereof, from a complex sample. By "complex sample" is intended any sample having DNA from more than one species of organism. In specific embodiments, the complex sample is an environmental sample, a biological sample, or a metagenomic sample. As used herein, the term "metagenome" or "metagenomic" refers to the collective genomes of all microorganisms present in a given habitat (Handelsman et al., (1998) *Chem. Biol.* 5: R245-R249; Microbial Metagenomics, Metatranscriptomics, and Metaproteomics. Methods in Enzymology vol. 531 DeLong, ed. (2013)). Environmental samples can be from soil, rivers, ponds, lakes, industrial wastewater, seawater, forests, agricultural lands on which crops are growing or have grown, or any other source having biodiversity. Complex samples also include colonies or cultures of microorganisms that are grown, collected in bulk, and pooled for storage and DNA preparation. In certain embodiments, complex samples are selected based on expected biodiversity that will allow for identification of gene sequences, and variants thereof.

The method disclosed herein does not require purified samples of single organisms but rather is able to identify homologous sequences directly from uncharacterized mixes of prokaryotic populations; from soil, from crude samples, and samples that are collected and/or mixed and not subjected to any purification. In this manner, the methods described herein can identify gene sequences, and variants thereof, from unculturable organisms, or those organisms that are difficult to culture.

I. Genes of Interest

New gene sequences of interest, variants thereof, and variants of known gene sequences can be identified using the methods disclosed herein. As used herein, a "gene sequence of interest," "target sequence," or "target sequences" is intended to refer to a known gene sequence. Known genes of interest include cry genes (Hofte and Whiteley (1989) Microbiol. Rev. 53(2):242-255; U.S. Pat. Nos. 8,609,936 and 8,609,937; cyt genes (or other hemolytic toxin or pest control genes, such as those listed in U.S. Pat. No. 8,067,671); mtx (or other mosquitocidal) genes; Binary toxins (such as those listed in U.S. Pat. No. 7,655,838); VIPs (or other vegetative insecticidal proteins, such as those listed in U.S. Pat. No. 8,344,307); SIPs (or other soluble insecticidal proteins); herbicide resistance genes such as EPSPS; HPPD; 16S rRNA sequences; and housekeeping genes. In particular embodiments, the gene of interest is of agricultural importance, such as genes that confer resistance to diseases and pests, and/or tolerance to herbicides in plants. Genes of interest can also be of biological, industrial, or medical interest such as genes as for antibiotic biosynthesis and antibiotic resistance, or biosynthesis of enzymes or other factors involved in bioremediation, bioconversion, industrial processes, detoxification, biofuel production, or compounds having cytotoxic, immune system priming or other therapeutic activity. Table 1 provides examples of genes sequences that can be used in the methods and compositions disclosed herein. The sequences and references provided herein incorporated by reference. It is important to note that these sequences are provided merely as examples; any sequences can be used in the practice of the methods and compositions disclosed herein.

The methods disclosed herein can identify variants of known sequences from multiple gene families of interest. As used herein, the term variants can refer to homologs, orthologs, and paralogs. While the activity of a variant may be altered compared to the gene of interest, the variant should retain the functionality of the gene of interest. For example, a variant may have increased activity, decreased activity, different spectrum of activity (e.g. for an insecticidal toxin gene) or any other alteration in activity when compared to the gene of interest.

In general, "variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" or "wild type" polynucleotide or polypeptide comprises a naturally occurring nucleotide sequence or amino acid sequence, respectively. For polynucleotides, conservative variants include those sequences that, because of the degeneracy of the genetic code, encode the amino acid sequence native sequence of the gene of interest. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode the polypeptide of the gene of interest. Generally, variants of a particular polynucleotides disclosed herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide (e.g., a gene of interest) as determined by sequence alignment programs and parameters described elsewhere herein.

Variants of a particular polynucleotide disclosed herein (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides disclosed herein is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

A. Sequence Analysis

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE™ (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

The use of the term "polynucleotide" is not intended to limit the present disclosure to polynucleotides comprising DNA. Those of ordinary skill in the art will recognize that polynucleotides, can comprise ribonucleotides (RNA) and combinations of ribonucleotides and deoxyribonucleotides. Such deoxyribonucleotides and ribonucleotides include both naturally occurring molecules and synthetic analogues. The polynucleotides disclosed herein also encompass all forms of sequences including, but not limited to, single-stranded forms, double-stranded forms, hairpins, stem-and-loop structures, and the like.

II. Bait Sequences

The methods and compositions described herein employ bait sequences to capture genes of interest, or variants thereof, from complex samples. As used herein a "bait sequence" or "bait" refers to a polynucleotide designed to hybridize to a gene of interest, or variant thereof. In specific embodiments bait sequences are single stranded RNA sequences capable of hybridizing to a fragment of the gene of interest. For example, the RNA bait sequence can be complementary to the DNA sequence of a fragment of the gene sequence of interest. In some embodiments, the bait sequence is capable of hybridizing to a fragment of the gene of interest that is at least 50, at least 70, at least 90, at least 100, at least 110, at least 120, at least 130, at least 140, at least 150, at least 170, at least 200, at least 250, at least 400, at least 1000 contiguous nucleotides, and up to the full-length polynucleotide sequence of the gene of interest. The baits can be contiguous or sequential RNA or DNA sequences. In one embodiment, bait sequences are RNA sequences. RNA sequences cannot self-anneal and work to drive the hybridization.

In specific embodiments, baits are at least 50, at least 70, at least 90, at least 100, at least 110, at least 120, at least 130, at least 140, at least 150, at least 170, at least 200, or at least 250 contiguous polynucleotides. For example, the bait sequence can be 50-200 nt, 50-200 nt, 70-150 nt, 100-140 nt, or 110-130 nt in length. The baits can be labeled with any detectable label in order to detect and/or capture the first hybridization complex comprised of a bait sequence hybridized to a fragment of the gene of interest, or variant thereof. In certain embodiments, the bait sequences are labeled with biotin, a hapten, or an affinity tag or the bait sequences are generated using biotinylated primers, e.g., where the baits are generated by nick-translation labeling of purified target organism DNA with biotinylated deoxynucleotides. In cases where the bait sequences are biotinylated, the target DNA can be captured using a binding partner, streptavidin molecule, attached to a solid phase. In specific embodiments, the baits are biotinylated RNA baits of about 120 nt in length. The baits may include adapter oligonucleotides suitable for PCR amplification, sequencing, or RNA transcription. The baits may include an RNA promoter or are RNA molecules prepared from DNA containing an RNA promoter (e.g., a T7 RNA promoter). Alternatively, antibodies specific for the RNA-DNA hybrid can be used (see, for example, WO2013164319 A1). In some embodiments, baits can be designed to 16S DNA sequences, or any other phylogenetically differential sequence, in order to capture sufficient portions of the 16S DNA to estimate the distribution of bacterial genera present in the sample.

The bait sequences span substantially the entire sequence of the known gene. In some embodiments, the bait sequences are overlapping bait sequences. As used herein, "overlapping bait sequences" or "overlapping" refers to fragments of the gene of interest that are represented in more than one bait sequence. For example, any given 120 nt segment of a gene of interest can be represented by a bait sequence having a region complementary to nucleotides 1-60 of the fragment, another bait sequence having a region complementary to nucleotides 61-120 of the fragment, and a third bait sequence complementary to nucleotides 1-120. In some embodiments, at least 10, at least 30, at least 60, at least 90, or at least 120 nucleotides of each overlapping bait overlap with at least one other overlapping bait. In this manner, each nucleotide of a given gene of interest can be represented in at least 2 baits, which is referred to herein as being covered by at least 2×. Accordingly the method described herein can use baits or labeled baits described herein that cover any gene of interest by at least 2× or at least 3×.

Baits for multiple genes can be used concurrently to hybridize with sample DNA prepared from a complex mixture. For example, if a given complex sample is to be screened for variants of multiple genes of interest, baits designed to each gene of interest can be combined in a bait pool prior to, or at the time of, mixing with prepared sample DNA. Accordingly, as used herein, a "bait pool" or "bait pools" refers to a mixture of baits designed to be specific for different fragments of an individual gene of interest and/or a mixture of baits designed to be specific for different genes of interest. "Distinct baits" refers to baits that are designed to be specific for different, or distinct, fragments of genes of interest.

Accordingly, in some embodiments, a method for preparing an RNA bait pool for the identification of genes of interest is provided. A given RNA bait pool can be specific for at least 1, at least 2, at least 10, at least 50, at least 100, at least 150, at least 200, at least 250, at least 300, at least 500, at least 750, at least 800, at least 900, at least 1,000, at least 1,500, at least 3,000, at least, 5,000, at least 10,000, at least 15,000, at least 20,000, at least 30,000, at least 40,000, at least 50,000, at least 55,000, at least 60,000, or any other number of genes of interest. As used herein, a bait that is specific for a gene of interest is designed to hybridize to the gene of interest. A bait can be specific for more than one gene of interest or variants of a gene of interest.

III. Methods of Isolating Genes of Interest, or Variants Thereof

Methods of the invention include preparation of bait sequences; preparation of complex mixture libraries; hybridization selection; sequencing; and analysis. Such methods are set forth in the experimental section in more detail. Additionally, see NucleoSpin® Soil User Manual, Rev. 03, U.S. Publication No. 20130230857; Gnirke et al. (2009) Nature Biotechnology 27:182-189; and SureSelect$^{XT}$® Target Enrichment System for Illumina Paired-End Sequencing Library Protocol, Version 1.6. All of which are herein incorporated by reference.

Methods of preparing complex samples include fractionation and extraction of environmental samples comprising soil, rivers, ponds, lakes, industrial wastewater, seawater, forests, agricultural lands on which crops are growing or have grown, or any other source having biodiversity. Fractionation can include filtration and/or centrifugation to preferentially isolate microorganisms. In some embodiments, complex samples are selected based on expected biodiversity that will allow for identification of gene sequences, and variants thereof. Further methods of preparing complex samples include colonies or cultures of microorganisms that are grown, collected in bulk, and pooled for storage and DNA preparation. In certain embodiments, complex samples are subjected to heat treatment or pasteurization to enrich for microbial spores that are resistant to heating. In some embodiments, the colonies or cultures are gown in media that enrich for specific types of microbes or microbes having specific structural or functional properties, such as cell wall composition, resistance to an antibiotic or other compound, or ability to grow on a specific nutrient mix or specific compound as a source of an essential element, such as carbon, nitrogen, phosphorus, or potassium.

In order to provide sample DNA for hybridization to baits as described elsewhere herein, the sample DNA must be prepared for hybridization. Preparing DNA from a complex sample for hybridization refers to any process wherein DNA from the sample is extracted and reduced in size sufficient for hybridization, herein referred to as fragmentation. For example, DNA can be extracted from any complex sample directly, or by isolating individual organisms from the complex sample prior to DNA isolation. In some embodiments, sample DNA is isolated from a pure culture or a mixed culture of microorganisms. DNA can be isolated by any method commonly known in the art for isolation of DNA from environmental or biological samples (see, e.g. Schneegurt et al. (2003) Current Issues in Molecular Biology 5:1-8; Zhou et al. (1996) Applied and Enicronmental Microbiology 62:316-322), including, but not limited to, the NucleoSpin® Soil genomic DNA preparation kit (Macherey-Nagel GmbH & Co., Distributed in the US by Clontech. In one embodiment, extracted DNA can be enriched for any desired source of sample DNA. For example, extracted DNA can be enriched for prokaryotic DNA by amplification. As used herein, the term "enrich" or "enriched" refers to the process of increasing the concentration of a specific target DNA population. For example, DNA can be enriched by amplification, such as by PCR, such that the target DNA population is increased about 1.5 fold, about 2 fold, about 3 fold, about 5 fold, about 10 fold, about 15 fold, about 30 fold, about 50 fold, or about 100 fold. In certain embodiments, sample DNA is enriched by using 16S amplification.

In some embodiments, after DNA is extracted from a complex sample, the extracted DNA is prepared for hybridization by fragmentation (e.g., by shearing) and/or end-labeling. End-labeling can use any end labels that are suitable for indexing, sequencing, or PCR amplification of the DNA. The fragmented sample DNA may be about 100-1000, 100-500, 125-400, 150-300, 200-2000, 100-3000, at least 100, at least 250, at least 200, at least 250, at least 300, or about 250 nucleotides in length. The detectable label may be, for example, biotin, a hapten, or an affinity tag. Thus, in certain embodiments, sample DNA is sheared and the ends of the sheared DNA fragments are repaired to yield blunt-ended fragments with 5'-phosphorylated ends. Sample DNA can further have a 3'-dA overhang prior to ligation to indexing-specific adaptors. Such ligated DNA can be purified and amplified using PCR in order to yield the prepared sample DNA for hybridization. In other embodiments, the sample DNA is prepared for hybridization by shearing, adaptor ligation, amplification, and purification.

In some embodiments, RNA is prepared from complex samples. RNA isolated from complex samples contains genes expressed by the organisms or groups of organisms in a particular environment, which can have relevance to the physiological state of the organism(s) in that environment, and can provide information about what biochemical pathways are active in the particular environment (e.g. Booijink et al. 2010. Applied and Environmental Microbiology 76: 5533-5540). RNA so prepared can be reverse-transcribed into DNA for hybridization, amplification, and sequence analysis.

Baits can be mixed with prepared sample DNA prior to hybridization by any means known in the art. The amount of baits added to the sample DNA should be sufficient to bind fragments of a gene of interest, or variant thereof. In some embodiments, a greater amount of baits is added to the mixture compared to the amount of sample DNA. The ratio of bait to sample DNA for hybridization can be about 1:4, about 1:3, about 1:2, about 1:1.8, about 1:1.6, about 1:1.4, about 1:1.2, about 1:1, about 2:1, about 3:1, about 4:1, about 5:1, about 10:1, about 20:1, about 50:1, or about 100:1.

While hybridization conditions may vary, hybridization of such bait sequences may be carried out under stringent conditions. By "stringent conditions" or "stringent hybridization conditions" is intended conditions under which the bait will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the bait can be identified (homologous probing). Alternatively, stringency conditions can be adjusted to allow some mismatching in sequences so that lower degrees of similarity are detected (heterologous probing). In specific embodiments, the prepared sample DNA is hybridized to the baits for 16-24 hours at 65° C.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short baits (e.g., 10 to 50 nucleotides) and at least about 60° C. for long baits (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the Tm can be approximated from the equation of Meinkoth and Wahl (1984) Anal. Biochem. 138:267-284: $Tm=81.5° C.+16.6 (\log M)+0.41 (\% GC)-0.61 (\% form)-500/L$; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched bait. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is optimal to increase the SSC concentration so that a higher temperature can be used. An extensive guide to the hybridization of nucleic acids is found in Tijssen (1993) Laboratory Techniques in Biochemistry and Molecular Biology—Hybridization with Nucleic Acid Probes, Part I, Chapter 2 (Elsevier, New York); and Ausubel et al., eds. (1995) Current Protocols in Molecular Biology, Chapter 2 (Greene Publishing and Wiley-Interscience, New York). See Sambrook et al. (1989) Molecular Cloning: A Laboratory Manual (2d ed., Cold Spring Harbor Laboratory Press, Plainview, N.Y.).

As used herein, a hybridization complex refers to sample DNA fragments hybridizing to a bait. Following hybridization, the labeled baits can be separated based on the presence of the detectable label, and the unbound sequences are removed under appropriate wash conditions that remove the nonspecifically bound DNA and unbound DNA, but do not substantially remove the DNA that hybridizes specifically. The hybridization complex can be captured and purified from non-binding baits and sample DNA fragments. For example, the hybridization complex can be captured by using a streptavidin molecule attached to a solid phase, such as a bead or a magnetic bead. In such embodiments, the hybridization complex captured onto the streptavidin coated bead can be selected by magnetic bead selection. The captured sample DNA fragment can then be amplified and index tagged for multiplex sequencing. As used herein, "index tagging" refers to the addition of a known polynucleotide sequence in order to track the sequence or provide a template for PCR. Index tagging the captured sample DNA sequences can identify the DNA source in the case that multiple pools of captured and indexed DNA are sequenced together. As used herein, an "enrichment kit" or "enrichment kit for multiplex sequencing" refers to a kit designed with reagents and instructions for preparing DNA from a complex sample and hybridizing the prepared DNA with labeled baits. In certain embodiments, the enrichment kit further provides reagents and instructions for capture and purification of the hybridization complex and/or amplification of any captured fragments of the genes of interest. In specific embodiments, the enrichment kit is the SureSelect$^{XT}$® Target Enrichment System for Illumina Paired-End Sequencing Library Protocol, Version 1.6.

Alternatively, the DNA from multiple complex samples can be indexed and amplified before hybridization. In such embodiments, the enrichment kit can be the SureSelect$^{XT2}$® Target Enrichment System for Illumina Multiplexed Sequencing Protocol, Version D.0

Following hybridization, the captured target organism DNA can be sequenced by any means known in the art. Sequencing of nucleic acids isolated by the methods described herein is, in certain embodiments, carried out using massively parallel short-read sequencing systems such as those provided by Illumina®, Inc. (1-HiSeq®1000, 1-HiSeq® 2000, HiSeq® 2500, Gnome Analyzers, MiSeq® systems), Applied Biosystems™ Life Technologies (ABI PRISM® Sequence detection systems, SOLiD™ System, Ion PGM™ Sequencer, Ion Proton™ Sequencer), because the read out generates more bases of sequence per sequencing unit than other sequencing methods that generate fewer but longer reads. Sequencing can also be carried out by methods generating longer reads, such as those provided by Oxford Nanopore Technologies® (GridiON®, MiniON®) or Pacific Biosciences (Pachio RS II) Sequencing can also be carried out by standard Sanger dideoxy terminator sequencing methods and devices, or on other sequencing instruments, further as those described in, for example, U.S. patents and patent applications U.S. Pat. Nos. 5,888,737, 6,175,002, 5,695,934, 6,140,489, 5,863,722, 2007/007991, 2009/0247414, 2010/01 11768 and PCT application WO2007/123744 each of which is incorporated herein by reference in its entirety.

Sequences can be assembled by any means known in the art. The sequences of individual fragments of genes of interest can be assembled to identify the full length sequence of the gene of interest, or variant thereof. In some embodiments, sequences are assembled using the CLCBio suite of bioinformatics tools. Following assembly, sequences of genes of interest, or variants thereof, are searched (e.g., sequence similarity search) against a database of known sequences including those of the genes of interest in order to identify the gene of interest, or variant thereof. In this manner, new variants (i.e., homologs) of genes of interest can be identified from complex samples.

IV. Kits for Identification of a Gene of Interest, or Variant Thereof.

Kits are provided for identifying genes of interest or variants thereof, by the methods disclosed herein. The kits include a bait pool or RNA bait pool, or reagents suitable for producing a bait pool specific for a gene of interest, along with other reagents, such as a solid phase containing a binding partner of any detectable label on the baits. In specific embodiments, the detectable label is biotin and the binding partner streptavidin or streptavidin adhered to magnetic beads. The kits may also include solutions for hybridization, washing, or eluting of the DNA/solid phase compositions described herein, or may include a concentrate of such solutions.

TABLE 1

Exemplary Target Gene and Polynucleotides

| Name | Acc No. | NCBI Protein | NCBI Nuc | Authors | Year | Source Strain |
|---|---|---|---|---|---|---|
| Cry1Aa1 | AAA22353 | 142765 | 142764 | Schnepf et al | 1985 | Bt kurstaki HD1 |
| Cry1Aa2 | AAA22552 | 551713 | 143100 | Shibano et al | 1985 | Bt sotto |
| Cry1Aa3 | BAA00257 | 216284 | 216283 | Shimizu et al | 1988 | Bt aizawai IPL7 |
| Cry1Aa4 | CAA31886 | 40267 | 40266 | Masson et al | 1989 | Bt entomocidus |
| Cry1Aa5 | BAA04468 | 535781 | 506190 | Udayasuriyan et al | 1994 | Bt Fu-2-7 |
| Cry1Aa6 | AAA86265 | 1171233 | 1171232 | Masson et al | 1994 | Bt kurstaki NRD-12 |
| Cry1Aa7 | AAD46139 | 5669035 | 5669034 | Osman et al | 1999 | Bt C12 |
| Cry1Aa8 | I26149 | | | Liu | 1996 | |
| Cry1Aa9 | BAA77213 | 4666284 | 4666283 | Nagamatsu et al | 1999 | Bt dendrolimus T84A1 |
| Cry1Aa10 | AAD55382 | 5901703 | 5901702 | Hou and Chen | 1999 | Bt kurstaki HD-1-02 |
| Cry1Aa11 | CAA70856 | 6687073 | 6687072 | Tounsi et al | 1999 | Bt kurstaki |
| Cry1Aa12 | AAP80146 | 32344731 | 32344730 | Yao et al | 2001 | Bt Ly30 |
| Cry1Aa13 | AAM44305 | 21239436 | 21239435 | Zhong et al | 2002 | Bt sotto |
| Cry1Aa14 | AAP40639 | 37781497 | 37781496 | Ren et al | 2002 | unpublished |
| Cry1Aa15 | AAY66993 | 67089177 | 67089176 | Sauka et al | 2005 | Bt INTA Mol-12 |
| Cry1Aa16 | HQ439776 | | | Liu et al | 2010 | Bt Ps9-E2 |

TABLE 1-continued

Exemplary Target Gene and Polynucleotides

| Name | Acc No. | NCBI Protein | NCBI Nuc | Authors | Year | Source Strain |
|---|---|---|---|---|---|---|
| Cry1Aa17 | HQ439788 | | | Liu et al | 2010 | Bt PS9-C12 |
| Cry1Aa18 | HQ439790 | | | Liu et al | 2010 | Bt PS9-D12 |
| Cry1Aa19 | HQ685121 | 337732098 | 337732097 | Li & Luo | 2011 | Bt LS-R-21 |
| Cry1Aa20 | JF340156 | | | Kumari & Kaur | 2011 | Bt SK-798 |
| Cry1Aa21 | JN651496 | | | Li Yuhong | 2011 | Bt LTS-209 |
| Cry1Aa22 | KC158223 | | | El Khoury et al | 2013 | Bt Lip |
| Cry1Ab1 | AAA22330 | 142720 | 142719 | Wabiko et al | 1986 | Bt berliner 1715 |
| Cry1Ab2 | AAA22613 | 143227 | 143226 | Thorne et al | 1986 | Bt kurstaki |
| Cry1Ab3 | AAA22561 | 143124 | 143123 | Geiser et al | 1986 | Bt kurstaki HD1 |
| Cry1Ab4 | BAA00071 | 216280 | 216279 | Kondo et al | 1987 | Bt kurstaki HD1 |
| Cry1Ab5 | CAA28405 | 40255 | 40254 | Hofte et al | 1986 | Bt berliner 1715 |
| Cry1Ab6 | AAA22420 | 142886 | 142885 | Hefford et al | 1987 | Bt kurstaki NRD-12 |
| Cry1Ab7 | CAA31620 | 40278 | 40277 | Haider & Ellar | 1988 | Bt aizawai IC1 |
| Cry1Ab8 | AAA22551 | 143099 | 143098 | Oeda et al | 1987 | Bt aizawai IPL7 |
| Cry1Ab9 | CAA38701 | 40273 | 40272 | Chak & Jen | 1993 | Bt aizawai HD133 |
| Cry1Ab10 | A29125 | | | Fischhoff et al | 1987 | Bt kurstaki HD1 |
| Cry1Ab11 | I12419 | | | Ely & Tippett | 1995 | Bt A20 |
| Cry1Ab12 | AAC64003 | 3746545 | 3746544 | Silva-Werneck et al | 1998 | Bt kurstaki S93 |
| Cry1Ab13 | AAN76494 | 25990352 | 25990351 | Tan et al | 2002 | Bt c005 |
| Cry1Ab14 | AAG16877 | 10440886 | 10440885 | Meza-Basso & Theoduloz | 2000 | Native Chilean Bt |
| Cry1Ab15 | AAO13302 | 27436100 | 27436098 | Li et al | 2001 | Bt B-Hm-16 |
| Cry1Ab16 | AAK55546 | 14190061 | 14190060 | Yu et al | 2002 | Bt AC-11 |
| Cry1Ab17 | AAT46415 | 48734426 | 48734425 | Huang et al | 2004 | Bt WB9 |
| Cry1Ab18 | AAQ88259 | 37048803 | 37048802 | Stobdan et al | 2004 | Bt |
| Cry1Ab19 | AAW31761 | 56900936 | 56900935 | Zhong et al | 2005 | Bt X-2 |
| Cry1Ab20 | ABB72460 | 82395049 | 82395048 | Liu et al | 2006 | BtC008 |
| Cry1Ab21 | ABS18384 | 151655610 | 151655609 | Swiecicka et al | 2007 | Bt IS5056 |
| Cry1Ab22 | ABW87320 | 159024156 | 159024155 | Wu and Feng | 2008 | BtS2491Ab |
| Cry1Ab23 | HQ439777 | | | Liu et al | 2010 | Bt N32-2-2 |
| Cry1Ab24 | HQ439778 | | | Liu et al | 2010 | Bt HD12 |
| Cry1Ab25 | HQ685122 | 337732100 | 337732099 | Li & Luo | 2011 | Bt LS-R-30 |
| Cry1Ab26 | HQ847729 | 320090245 | 320090244 | Prathap Reddy et al | 2011 | DOR BT-1 |
| Cry1Ab27 | JN135249 | | | Ammouneh et al | 2011 | |
| Cry1Ab28 | JN135250 | | | Ammouneh et al | 2011 | |
| Cry1Ab29 | JN135251 | | | Ammouneh et al | 2011 | |
| Cry1Ab30 | JN135252 | | | Ammouneh et al | 2011 | |
| Cry1Ab31 | JN135253 | | | Ammouneh et al | 2011 | |
| Cry1Ab32 | JN135254 | | | Ammouneh et al | 2011 | |
| Cry1Ab33 | AAS93798 | | | Li et al | 2012 | Bt kenyae K3 |
| Cry1Ab34 | KC156668 | | | Sampson et al | 2012 | |
| Cry1Ab-like | AAK14336 | 13173238 | 13173237 | Nagarathinam et al | 2001 | Bt kunthala RX24 |
| Cry1Ab-like | AAK14337 | 13173240 | 13173239 | Nagarathinam et al | 2001 | Bt kunthala RX28 |
| Cry1Ab-like | AAK14338 | 13173242 | 13173241 | Nagarathinam et al | 2001 | Bt kunthala RX27 |
| Cry1Ab-like | ABG88858 | 110734449 | 110734448 | Lin et al | 2006 | Bt ly4a3 |
| Cry1Ac1 | AAA22331 | | | Adang et al | 1985 | Bt kurstaki HD73 |
| Cry1Ac2 | AAA22338 | | | Von Tersch et al | 1991 | Bt kenyae |
| Cry1Ac3 | CAA38098 | | | Dardenne et al | 1990 | Bt BTS89A |
| Cry1Ac4 | AAA73077 | | | Feitelson | 1991 | Bt kurstaki PS85A1 |
| Cry1Ac5 | AAA22339 | | | Feitelson | 1992 | Bt kurstaki PS81GG |
| Cry1Ac6 | AAA86266 | | | Masson et al | 1994 | Bt kurstaki NRD-12 |
| Cry1Ac7 | AAB46989 | | | Herrera et al | 1994 | Bt kurstaki HD73 |
| Cry1Ac8 | AAC44841 | | | Omolo et al | 1997 | Bt kurstaki HD73 |
| Cry1Ac9 | AAB49768 | | | Gleave et al | 1992 | Bt DSIR732 |
| Cry1Ac10 | CAA05505 | | | Sun | 1997 | Bt kurstaki YBT-1520 |
| Cry1Ac11 | CAA10270 | | | Makhdoom & Riazuddin | 1998 | |
| Cry1Ac12 | I12418 | | | Ely & Tippett | 1995 | Bt A20 |
| Cry1Ac13 | AAD38701 | | | Qiao et al | 1999 | Bt kurstaki HD1 |
| Cry1Ac14 | AAQ06607 | | | Yao et al | 2002 | Bt Ly30 |
| Cry1Ac15 | AAN07788 | | | Tzeng et al | 2001 | Bt from Taiwan |
| Cry1Ac16 | AAU87037 | | | Zhao et al | 2005 | Bt H3 |
| Cry1Ac17 | AAX18704 | | | Hire et al | 2005 | Bt kenyae HD549 |
| Cry1Ac18 | AAY88347 | | | Kaur & Allam | 2005 | Bt SK-729 |
| Cry1Ac19 | ABD37053 | | | Gao et al | 2005 | Bt C-33 |
| Cry1Ac20 | ABB89046 | | | Tan et al | 2005 | |
| Cry1Ac21 | AAY66992 | | | Sauka et al | 2005 | INTA Mo1-12 |
| Cry1Ac22 | ABZ01836 | | | Zhang & Fang | 2008 | Bt W015-1 |
| Cry1Ac23 | CAQ30431 | | | Kashyap et al | 2008 | Bt |
| Cry1Ac24 | ABL01535 | | | Arango et al | 2008 | Bt 146-158-01 |
| Cry1Ac25 | FJ513324 | 237688242 | 237688241 | Guan et al | 2011 | Bt Tm37-6 |
| Cry1Ac26 | FJ617446 | 256003038 | 256003037 | Guan et al | 2011 | Bt Tm41-4 |
| Cry1Ac27 | FJ617447 | 256003040 | 256003039 | Guan et al | 2011 | Bt Tm44-1B |
| Cry1Ac28 | ACM90319 | | | Li et al | 2009 | Bt Q-12 |
| Cry1Ac29 | DQ438941 | | | Diego Sauka | 2009 | INTA TA24-6 |
| Cry1Ac30 | GQ227507 | | | Zhang et al | 2010 | Bt S1478-1 |
| Cry1Ac31 | GU446674 | 319433505 | | Zhao et al | 2010 | Bt S3299-1 |

TABLE 1-continued

Exemplary Target Gene and Polynucleotides

| Name | Acc No. | NCBI Protein | NCBI Nuc | Authors | Year | Source Strain |
|---|---|---|---|---|---|---|
| Cry1Ac32 | HM061081 | | | Lu et al | 2010 | Bt ZQ-89 |
| Cry1Ac33 | GQ866913 | 306977639 | 306977638 | Kaur & Meena | 2011 | Bt SK-711 |
| Cry1Ac34 | HQ230364 | 314906994 | | Kaur & Kumari | 2010 | Bt SK-783 |
| Cry1Ac35 | JF340157 | | | Kumari & Kaur | 2011 | Bt SK-784 |
| Cry1Ac36 | JN387137 | | | Kumari & Kaur | 2011 | Bt SK-958 |
| Cry1Ac37 | JQ317685 | | | Kumari & Kaur | 2011 | Bt SK-793 |
| Cry1Ac38 | ACC86135 | | | Lin et al | 2008 | Bt LSZ9408 |
| Cry1Ad1 | AAA22340 | | | Feitelson | 1993 | Bt aizawai PS81I |
| Cry1Ad2 | CAA01880 | | | Anonymous | 1995 | Bt PS81RR1 |
| Cry1Ae1 | AAA22410 | | | Lee & Aronson | 1991 | Bt alesti |
| Cry1Af1 | AAB82749 | | | Kang et al | 1997 | Bt NT0423 |
| Cry1Ag1 | AAD46137 | | | Mustafa | 1999 | |
| Cry1Ah1 | AAQ14326 | | | Tan et al | 2000 | |
| Cry1Ah2 | ABB76664 | | | Qi et al | 2005 | Bt alesti |
| Cry1Ah3 | HQ439779 | | | Liu et al | 2010 | Bt S6 |
| Cry1Ai1 | AA039719 | | | Wang et al | 2002 | |
| Cry1Ai2 | HQ439780 | | | Liu et al | 2010 | Bt SC6H8 |
| Cry1A-like | AAK14339 | | | Nagarathinam et al | 2001 | Bt kunthala nags3 |
| Cry1Ba1 | CAA29898 | | | Brizzard & Whiteley | 1988 | Bt thuringiensis HD2 |
| Cry1Ba2 | CAA65003 | | | Soetaert | 1996 | Bt entomocidus HD110 |
| Cry1Ba3 | AAK63251 | | | Zhang et al | 2001 | |
| Cry1Ba4 | AAK51084 | | | Nathan et al | 2001 | Bt entomocidus HD9 |
| Cry1Ba5 | AB020894 | | | Song et al | 2007 | Bt sfw-12 |
| Cry1Ba6 | ABL60921 | | | Martins et al | 2006 | Bt 5601 |
| Cry1Ba7 | HQ439781 | | | Liu et al | 2010 | Bt N17-37 |
| Cry1Bb1 | AAA22344 | | | Donovan et al | 1994 | Bt EG5847 |
| Cry1Bb2 | HQ439782 | | | Liu et al | 2010 | Bt WBT-2 |
| Cry1Bc1 | CAA86568 | | | Bishop et al | 1994 | Bt morrisoni |
| Cry1Bd1 | AAD10292 | | | Kuo et al | 2000 | Bt wuhanensis HD525 |
| Cry1Bd2 | AAM93496 | | | Isakova et al | 2002 | Bt 834 |
| Cry1Be1 | AAC32850 | | | Payne et al | 1998 | Bt PS158C2 |
| Cry1Be2 | AAQ52387 | | | Baum et al | 2003 | |
| Cry1Be3 | ACV96720 | 259156864 | | Sun et al | 2010 | Bt g9 |
| Cry1Be4 | HM070026 | | | Shu et al | 2010 | |
| Cry1Bf1 | CAC50778 | | | Arnaut et al | 2001 | |
| Cry1Bf2 | AAQ52380 | | | Baum et al | 2003 | |
| Cry1Bg1 | AA039720 | | | Wang et al | 2002 | |
| Cry1Bh1 | HQ589331 | 315076091 | | Lira et al | 2010 | Bt PS46L |
| Cry1Bi1 | KC156700 | | | Sampson et al | 2012 | |
| Cry1Ca1 | CAA30396 | | | Honee et al | 1988 | Bt entomocidus 60.5 |
| Cry1Ca2 | CAA31951 | | | Sanchis et al | 1989 | Bt aizawai 7.29 |
| Cry1Ca3 | AAA22343 | | | Feitelson | 1993 | Bt aizawai PS81I |
| Cry1Ca4 | CAA01886 | | | Van Mellaert et al | 1990 | Bt entomocidus HD110 |
| Cry1Ca5 | CAA65457 | | | Strizhov | 1996 | Bt aizawai 7.29 |
| Cry1Ca6 [1] | AAF37224 | | | Yu et al | 2000 | Bt AF-2 |
| Cry1Ca7 | AAG50438 | | | Aixing et al | 2000 | Bt J8 |
| Cry1Ca8 | AAM00264 | | | Chen et al | 2001 | Bt c002 |
| Cry1Ca9 | AAL79362 | | | Kao et al | 2003 | Bt G10-01A |
| Cry1Ca10 | AAN16462 | | | Lin et al | 2003 | Bt E05-20a |
| Cry1Ca11 | AAX53094 | | | Cai et al | 2005 | Bt C-33 |
| Cry1Ca12 | HM070027 | | | Shu et al | 2010 | |
| Cry1Ca13 | HQ412621 | 312192962 | | Li & Luo | 2010 | Bt LB-R-78 |
| Cry1Ca14 | JN651493 | | | Li Yuhong | 2011 | Bt LTS-38 |
| Cry1Cb1 | M97880 | | | Kalman et al | 1993 | Bt galleriae HD29 |
| Cry1Cb2 | AAG35409 | | | Song et al | 2000 | Bt c001 |
| Cry1Cb3 | ACD50894 | | | Huang et al | 2008 | Bt 087 |
| Cry1Cb-like | AAX63901 | | | Thammasittirong et al | 2005 | Bt TA476-1 |
| Cry1Da1 | CAA38099 | | | Hofte et al | 1990 | Bt aizawai HD68 |
| Cry1Da2 | 176415 | | | Payne & Sick | 1997 | |
| Cry1Da3 | HQ439784 | | | Liu et al | 2010 | Bt HD12 |
| Cry1Db1 | CAA80234 | | | Lambert | 1993 | Bt BTS00349A |
| Cry1Db2 | AAK48937 | | | Li et al | 2001 | Bt B-Pr-88 |
| Cry1Dc1 | ABK35074 | | | Lertwiriyawong et al | 2006 | Bt JC291 |
| Cry1Ea1 | CAA37933 | | | Visser et al | 1990 | Bt kenyae 4F1 |
| Cry1Ea2 | CAA39609 | | | Bosse et al | 1990 | Bt kenyae |
| Cry1Ea3 | AAA22345 | | | Feitelson | 1991 | Bt kenyae PS81F |
| Cry1Ea4 | AAD04732 | | | Barboza-Corona et al | 1998 | Bt kenyae LBIT-147 |
| Cry1Ea5 | A15535 | | | Botterman et al | 1994 | |
| Cry1Ea6 | AAL50330 | | | Sun et al | 1999 | Bt YBT-032 |
| Cry1Ea7 | AAW72936 | | | Huehne et al | 2005 | Bt JC190 |
| Cry1Ea8 | ABX11258 | | | Huang et al | 2007 | Bt HZM2 |
| Cry1Ea9 | HQ439785 | | | Liu et al | 2010 | Bt S6 |
| Cry1Ea10 | ADR00398 | | | Goncalves et al | 2010 | Bt BR64 |
| Cry1Ea11 | JQ652456 | | | Lin Qunxin et al | 2012 | Bt |
| Cry1Ea12 | KF601559 | | | Baonan He | 2013 | Bt strain V4 |

TABLE 1-continued

Exemplary Target Gene and Polynucleotides

| Name | Acc No. | NCBI Protein | NCBI Nuc | Authors | Year | Source Strain |
|---|---|---|---|---|---|---|
| Cry1Eb1 | AAA22346 | | | Feitelson | 1993 | Bt aizawai PS81A2 |
| Cry1Fal | AAA22348 | | | Chambers et al | 1991 | Bt aizawai EG6346 |
| Cry1Fa2 | AAA22347 | | | Feitelson | 1993 | Bt aizawai PS81I |
| Cry1Fa3 | HM070028 | | | Shu et al | 2010 | |
| Cry1Fa4 | HM439638 | | | Liu et al | 2010 | Bt mo3-D10 |
| Cry1Fb1 | CAA80235 | | | Lambert | 1993 | Bt BTS00349A |
| Cry1Fb2 | BAA25298 | | | Masuda & Asano | 1998 | Bt morrisoni INA67 |
| Cry1Fb3 | AAF21767 | | | Song et al | 1998 | Bt morrisoni |
| Cry1Fb4 | AAC10641 | | | Payne et al | 1997 | |
| Cry1Fb5 | AA013295 | | | Li et al | 2001 | Bt B-Pr-88 |
| Cry1Fb6 | ACD50892 | | | Huang et al | 2008 | Bt 012 |
| Cry1Fb1 | ACD50893 | | | Huang et al | 2008 | Bt 087 |
| Cry1Ga1 | CAA80233 | | | Lambert | 1993 | Bt BTS0349A |
| Cry1Ga2 | CAA70506 | | | Shevelev et al | 1997 | Bt wuhanensis |
| Cry1Gb1 | AAD10291 | | | Kuo & Chak | 1999 | Bt wuhanensis HD525 |
| Cry1Gb2 | AA013756 | | | Li et al | 2000 | Bt B-Pr-88 |
| Cry1Gc1 | AAQ52381 | | | Baum et al | 2003 | |
| Cry1Ha1 | CAA80236 | | | Lambert | 1993 | Bt BTS02069AA |
| Cry1Hb1 | AAA79694 | | | Koo et al | 1995 | Bt morrisoni BF190 |
| Cry1Hb2 | HQ439786 | | | Liu et al | 2010 | Bt WBT-2 |
| Cry1H-like | AAF01213 | | | Srifah et al | 1999 | Bt JC291 |
| Cry1Ia1 | CAA44633 | | | Tailor et al | 1992 | Bt kurstaki |
| Cry1Ia2 | AAA22354 | | | Gleave et al | 1993 | Bt kurstaki |
| Cry1Ia3 | AAC36999 | | | Shin et al | 1995 | Bt kurstaki HD1 |
| Cry1Ia4 | AAB00958 | | | Kostichka et al | 1996 | Bt AB88 |
| Cry1Ia5 | CAA70124 | | | Selvapandiyan | 1996 | Bt 61 |
| Cry1Ia6 | AAC26910 | | | Zhong et al | 1998 | Bt kurstaki S101 |
| Cry1Ia7 | AAM73516 | | | Porcar et al | 2000 | Bt |
| Cry1Ia8 | AAK66742 | | | Song et al | 2001 | |
| Cry1Ia9 | AAQ08616 | | | Yao et al | 2002 | Bt Ly30 |
| Cry1Ia10 | AAP86782 | | | Espindola et al | 2003 | Bt thuringiensis |
| Cry1Ia11 | CAC85964 | | | Tounsi et al | 2003 | Bt kurstaki BNS3 |
| Cry1Ia12 | AAV53390 | | | Grossi de Sa et al | 2005 | Bt |
| Cry1Ia13 | ABF83202 | | | Martins et al | 2006 | Bt |
| Cry1Ia14 | ACG63871 | | | Liu & Guo | 2008 | Btl 1 |
| Cry1Ia15 | FJ617445 | 256003036 | 256003035 | Guan et al | 2011 | Bt E-1B |
| Cry1Ia16 | FJ617448 | 256003042 | 256003041 | Guan et al | 2011 | Bt E-1A |
| Cry1Ia17 | GU989199 | | | Li et al | 2010 | Bt MX2 |
| Cry1Ia18 | ADK23801 | 300492624 | | Li et al | 2010 | Bt MX9 |
| Cry1Ial9 | HQ439787 | | | Liu et al | 2010 | Bt SC6H6 |
| Cry1Ia20 | JQ228426 | | | Zhao Can | 2011 | Bt wulH-3 |
| Cry1Ia21 | JQ228424 | | | Zhao Can | 2011 | Bt youlD-9 |
| Cry1Ia22 | JQ228427 | | | Zhao Can | 2011 | Bt wulE-3 |
| Cry1Ia23 | JQ228428 | | | Zhao Can | 2011 | Bt wulE-4 |
| Cry1Ia24 | JQ228429 | | | Zhao Can | 2011 | Bt wu2B-6 |
| Cry1Ia25 | JQ228430 | | | Zhao Can | 2011 | Bt wu2G-11 |
| Cry1Ia26 | JQ228431 | | | Zhao Can | 2011 | Bt wu2G-12 |
| Cry1Ia27 | JQ228432 | | | Zhao Can | 2011 | Bt you2D-3 |
| Cry1Ia28 | JQ228433 | | | Zhao Can | 2011 | Bt you2E-3 |
| Cry1Ia29 | JQ228434 | | | Zhao Can | 2011 | Bt you2F-3 |
| Cry1Ia30 | JQ317686 | | | Kumari & Kaur | 2011 | Bt 4J4 |
| Cry1Ia31 | JX944038 | | | Song et al | 2012 | Bt SC-7 |
| Cry1Ia32 | JX944039 | | | Song et al | 2012 | Bt SC-13 |
| Cry1Ia33 | JX944040 | | | Song et al | 2012 | Bt SC-51 |
| Cry11Ib1 | AAA82114 | | | Shin et al | 1995 | Bt entomocidus BP465 |
| Cry1Ib2 | ABW88019 | | | Guan et al | 2007 | Bt PP61 |
| Cry1Ib3 | ACD75515 | | | Liu & Guo | 2008 | Bt GS8 |
| Cry1Ib4 | HM051227 | 301641366 | | Zhao et al | 2010 | Bt BF-4 |
| Cry1Ib5 | HM070028 | | | Shu et al | 2010 | |
| Cry1Ib6 | ADK38579 | 300836937 | | Li et al | 2010 | Bt LB52 |
| Cry1Ib7 | JN571740 | | | Kumari & Kaur | 2011 | Bt SK-935 |
| Cry1Ib8 | JN675714 | | | Swamy et al | 2011 | |
| Cry1Ib9 | JN675715 | | | Swamy et al | 2011 | |
| Cry1Ib10 | JN675716 | | | Swamy et al | 2011 | |
| Cry1Ib11 | JQ228423 | | | Zhao Can | 2011 | Bt HD12 |
| Cry1Icl | AAC62933 | | | Osman et al | 1998 | Bt C18 |
| Cry1Ic2 | AAE71691 | | | Osman et al | 2001 | |
| Cry1Id1 | AAD44366 | | | Choi | 2000 | |
| Cry1Id2 | JQ228422 | | | Zhao Can | 2011 | Bt HD12 |
| Cry1Ie1 | AAG43526 | | | Song et al | 2000 | Bt BTC007 |
| Cry1Ie2 | HM439636 | | | Liu et al | 2010 | Bt T03B001 |
| Cry1Ie3 | KC156647 | | | Sampson et al | 2012 | |
| Cry1Ie4 | KC156681 | | | Sampson et al | 2012 | |
| Cry1If1 | AAQ52382 | | | Baum et al | 2003 | |
| Cry1Ig1 | KC156701 | | | Sampson et al | 2012 | |

TABLE 1-continued

Exemplary Target Gene and Polynucleotides

| Name | Acc No. | NCBI Protein | NCBI Nuc | Authors | Year | Source Strain |
|---|---|---|---|---|---|---|
| Cry1I-like | AAC31094 | | | Payne et al | 1998 | |
| Cry1I-like | ABG88859 | | | Lin & Fang | 2006 | Bt 1y4a3 |
| Cry1Ja1 | AAA22341 | | | Donovan | 1994 | Bt EG5847 |
| Cry1Ja2 | HM070030 | | | Shu et al | 2010 | |
| Cry1Ja3 | JQ228425 | | | Zhao Shiyuan | 2011 | Bt FH21 |
| Cry1Jb1 | AAA98959 | | | Von Tersch & Gonzalez | 1994 | Bt EG5092 |
| Cry1Jc1 | AAC31092 | | | Payne et al | 1998 | |
| Cry1Jc2 | AAQ52372 | | | Baum et al | 2003 | |
| Cry1Jd1 | CAC50779 | | | Arnaut et al | 2001 | Bt |
| Cry1Ka1 | AAB00376 | | | Koo et al | 1995 | Bt morrisoni BF190 |
| Cry1Ka2 | HQ439783 | | | Liu et al | 2010 | Bt WBT-2 |
| Cry1La1 | AAS60191 | | | Je et al | 2004 | Bt kurstaki K1 |
| Cry1La2 | HM070031 | | | Shu et al | 2010 | |
| Cry1Ma1 | FJ884067 | | | Noguera & Ibarra | 2010 | LBIT 1189 |
| Cry1Ma2 | KC156659 | | | Sampson et al | 2012 | |
| Cry1Na1 | KC156648 | | | Sampson et al | 2012 | |
| Cry1Nb1 | KC156678 | | | Sampson et al | 2012 | |
| Cry1-like | AAC31091 | | | Payne et al | 1998 | |
| Cry2Aa1 | AAA22335 | | | Donovan et al | 1989 | Bt kurstaki |
| Cry2Aa2 | AAA83516 | | | Widner & Whiteley | 1989 | Bt kurstaki HD1 |
| Cry2Aa3 | D86064 | | | Sasaki et al | 1997 | Bt sotto |
| Cry2Aa4 | AAC04867 | | | Misra et al | 1998 | Bt kenyae HD549 |
| Cry2Aa5 | CAA10671 | | | Yu & Pang | 1999 | Bt SL39 |
| Cry2Aa6 | CAA10672 | | | Yu & Pang | 1999 | Bt YZ71 |
| Cry2Aa7 | CAA10670 | | | Yu & Pang | 1999 | Bt CY29 |
| Cry2Aa8 | AAO13734 | | | Wei et al | 2000 | Bt Dongbei 66 |
| Cry2Aa9 | AAO13750 | | | Zhang et al | 2000 | |
| Cry2Aa10 | AAQ04263 | | | Yao et al | 2001 | |
| Cry2Aa11 | AAQ52384 | | | Baum et al | 2003 | |
| Cry2Aa12 | AB183671 | | | Tan et al | 2006 | Bt Rpp39 |
| Cry2Aa13 | ABL01536 | | | Arango et al | 2008 | Bt 146-158-01 |
| Cry2Aa14 | ACF04939 | | | Hire et al | 2008 | Bt HD-550 |
| Cry2Aa15 | JN426947 | | | Ammouneh et al | 2011 | Bt SSy77 |
| Cry2Aa16 | KF667522 | | | Baonan He | 2013 | Bt V4 |
| Cry2Aa17 | KF860848 | | | Guihua Chen et al | 2013 | |
| Cry2Ab1 | AAA22342 | | | Widner & Whiteley | 1989 | Bt kurstaki HD1 |
| Cry2Ab2 | CAA39075 | | | Dankocsik et al | 1990 | Bt kurstaki HD1 |
| Cry2Ab3 | AAG36762 | | | Chen et al | 1999 | Bt BTC002 |
| Cry2Ab4 | AAO13296 | | | Li et al | 2001 | Bt B-Pr-88 |
| Cry2Ab5 | AAQ04609 | | | Yao et al | 2001 | Bt ly30 |
| Cry2Ab6 | AAP59457 | | | Wang et al | 2003 | Bt WZ-7 |
| Cry2Ab7 | AAZ66347 | | | Udayasuriyan et al | 2005 | Bt 14-1 |
| Cry2Ab8 | ABC95996 | | | Huang et al | 2006 | Bt WB2 |
| Cry2Ab9 | ABC74968 | | | Zhang et al | 2005 | Bt LLB6 |
| Cry2Ab10 | ABM21766 | | | Lin et al | 2006 | Bt LyL |
| Cry2Ab11 | CAM84575 | | | Saleem et al | 2007 | Bt CMBL-BT1 |
| Cry2Ab12 | AB M21764 | | | Lin et al | 2007 | Bt LyD |
| Cry2Ab13 | ACG76120 | | | Zhu et al | 2008 | Bt ywc5-4 |
| Cry2Ab14 | ACG76121 | | | Zhu et al | 2008 | Bt Bts |
| Cry2Ab15 | HM037126 | 302634222 | 302634221 | Zhao et al | 2011 | Bt BF-4 |
| Cry2Ab16 | GQ866914 | 306977641 | 306977640 | Katara & Kaur | 2011 | SK-793 |
| Cry2Ab17 | HQ439789 | | | Liu et al | 2010 | Bt PS9-C12 |
| Cry2Ab18 | JN135255 | | | Ammouneh et al | 2011 | |
| Cry2Ab19 | JN135256 | | | Ammouneh et al | 2011 | |
| Cry2Ab20 | JN135257 | | | Ammouneh et al | 2011 | |
| Cry2Ab21 | JN135258 | | | Ammouneh et al | 2011 | |
| Cry2Ab22 | JN135259 | | | Ammouneh et al | 2011 | |
| Cry2Ab23 | JN135260 | | | Ammouneh et al | 2011 | |
| Cry2Ab24 | JN135261 | | | Ammouneh et al | 2011 | |
| Cry2Ab25 | JN415485 | | | Sevim et al | 2013 | Btk MnD |
| Cry2Ab26 | JN426946 | | | Ammouneh et al | 2011 | Bt SSy77 |
| Cry2Ab27 | JN415764 | 344055822 | 344055821 | Chankhamhaengdecha et al | 2011 | |
| Cry2Ab28 | JN651494 | | | Li Yuhong | 2011 | Bt LTS-7 |
| Cry2Ab29 | KF860847 | | | Guihua Chen et al | 2013 | |
| Cry2Ab30 | EU623976 | | | Lian Xu et al | 2013 | |
| Cry2Ac1 | CAA40536 | | | Aronson | 1991 | Bt shanghai S1 |
| Cry2Ac2 | AAG35410 | | | Song et al | 2000 | |
| Cry2Ac3 | AAQ52385 | | | Baum et al | 2003 | |
| Cry2Ac4 | ABC95997 | | | Huang et al | 2006 | Bt WB9 |
| Cry2Ac5 | ABC74969 | | | Zhang et al | 2005 | |
| Cry2Ac6 | ABC74793 | | | Xia et al | 2006 | Bt wuhanensis |
| Cry2Ac7 | CAL18690 | | | Saleem et al | 2008 | Bt SBSBT-1 |
| Cry2Ac 8 | CAM09325 | | | Saleem et al | 2007 | Bt CMBL-BT1 |
| Cry2Ac9 | CAM09326 | | | Saleem et al | 2007 | Bt CMBL-BT2 |
| Cry2Ac10 | ABN15104 | | | Bai et al | 2007 | Bt QCL-1 |

TABLE 1-continued

Exemplary Target Gene and Polynucleotides

| Name | Acc No. | NCBI Protein | NCBI Nuc | Authors | Year | Source Strain |
|---|---|---|---|---|---|---|
| Cry2Ac11 | CAM83895 | | | Saleem et al | 2007 | Bt HD29 |
| Cry2Ac12 | CAM83896 | | | Saleem et al | 2007 | Bt CMBL-BT3 |
| Cry2Ad1 | AAF09583 | | | Choi et al | 1999 | Bt BR30 |
| Cry2Ad2 | ABC86927 | | | Huang et al | 2006 | Bt WB10 |
| Cry2Ad3 | CAK29504 | | | Saleem et al | 2006 | Bt 5_2AcT(1) |
| Cry2Ad4 | CAM32331 | | | Saleem et al | 2007 | Bt CMBL-BT2 |
| Cry2Ad5 | CA078739 | | | Saleem et al | 2007 | Bt HD29 |
| Cry2Ae1 | AAQ52362 | | | Baum et al | 2003 | |
| Cry2Af1 | AB 030519 | | | Beard et al | 2007 | Bt C81 |
| Cry2Af2 | GQ866915 | 306977643 | 306977642 | Katara & Kaur | 2011 | SK-758 |
| Cry2Ag1 | ACH91610 | | | Zhu et al | 2008 | Bt JF19-2 |
| Cry2Ah1 | EU939453 | 218963751 | 218963750 | Zhang et al | 2011 | Bt SC6H8 |
| Cry2Ah2 | ACL80665 | | | Zhang et al | 2009 | Bt BRC-ZQL3 |
| Cry2Ah3 | GU073380 | 309274394 | 309274393 | Lixin Du | 2012 | HYW-8 |
| Cry2Ah4 | KC156702 | | | Sampson et al | 2012 | |
| Cry2Ai1 | FJ788388 | | 259166843 | Udayasuriyan et al | 2009 | Bt |
| Cry2Aj1 | | | | Zhicheng Shen | 2009 | |
| Cry2Ak1 | KC156660 | | | Sampson et al | 2012 | |
| Cry2Ba1 | KC156658 | | | Sampson et al | 2012 | |
| Cry2Ba2 | KF014123 | | | Guihua Chen et al | 2013 | |
| Cry3Aa1 | AAA22336 | | | Herrnstadt et al | 1987 | Bt san diego |
| Cry3Aa2 | AAA22541 | | | Sekar et al | 1987 | Bt tenebrionis |
| Cry3Aa3 | CAA68482 | | | Hofte et al | 1987 | |
| Cry3Aa4 | AAA22542 | | | McPherson et al | 1988 | Bt tenebrionis |
| Cry3Aa5 | AAA50255 | | | Donovan et al | 1988 | Bt morrisoni EG2158 |
| Cry3Aa6 | AAC43266 | | | Adams et al | 1994 | Bt tenebrionis |
| Cry3Aa7 | CAB41411 | | | Zhang et al | 1999 | Bt 22 |
| Cry3Aa8 | AAS79487 | | | Gao and Cai | 2004 | Bt YM-03 |
| Cry3Aa9 | AAW05659 | | | Bulla and Candas | 2004 | Bt UTD-001 |
| Cry3Aa10 | AAU29411 | | | Chen et al | 2004 | Bt 886 |
| Cry3Aa11 | AAW82872 | | | Kurt et al | 2005 | Bt tenebrionis Mm2 |
| Cry3Aa12 | ABY49136 | | | Sezen et al | 2008 | Bt tenebrionis |
| Cry3Ba1 | CAA34983 | | | Sick et al | 1990 | Bt tolworthi 43F |
| Cry3Ba2 | CAA00645 | | | Peferoen et al | 1990 | Bt PGSI208 |
| Cry3Ba3 | JQ397327 | | | Palma et al | 2011 | Bt |
| Cry3Bb1 | AAA22334 | | | Donovan et al | 1992 | Bt EG4961 |
| Cry3Bb2 | AAA74198 | | | Donovan et al | 1995 | Bt EG5144 |
| Cry3Bb3 | 115475 | | | Peferoen et al | 1995 | |
| Cry3Ca1 | CAA42469 | | | Lambert et al | 1992 | Bt kurstaki BtI109P |
| Cry4Aa1 | CAA68485 | | | Ward & Ellar | 1987 | Bt israelensis |
| Cry4Aa2 | BAA00179 | | | Sen et al | 1988 | Bt israelensis HD522 |
| Cry4Aa3 | CAD30148 | | | Berry et al | 2002 | Bt israelensis |
| Cry4Aa4 | AFB18317 | 376008213 | | Li et al | 2012 | Bti BRC-LLP29 |
| Cry4A-like | AAY96321 | | | Mahalakshmi et al | 2005 | Bt LDC-9 |
| Cry4Ba1 | CAA30312 | | | Chungjatpornchai et al | 1988 | Bt israelensis 4Q2-72 |
| Cry4Ba2 | CAA30114 | | | Tungpradubkul et al | 1988 | Bt israelensis |
| Cry4Ba3 | AAA22337 | | | Yamamoto et al | 1988 | Bt israelensis |
| Cry4Ba4 | BAA00178 | | | Sen et al | 1988 | Bt israelensis HD522 |
| Cry4Ba5 | CAD30095 | | | Berry et al | 2002 | Bt israelensis |
| Cry4Ba-like | ABC47686 | | | Mahalakshmi et al | 2005 | Bt LDC-9 |
| Cry4Ca1 | EU646202 | 194396263 | 194396262 | Shu et al | 2011 | Bt Y41 |
| Cry4Cb1 | FJ403208 | 234203282 | 234203281 | Zhu et al | 2010 | Bt HS18-l |
| Cry4Cb2 | FJ597622 | 256033943 | 256033942 | Zhu et al | 2011 | Bt Ywc2-8 |
| Cry4Cc1 | FJ403207 | 234203244 | 234203243 | Zhu et al | 2011 | Bt MC28 |
| Cry5Aa1 | AAA67694 | | | Narva et al | 1994 | Bt darmstadiensis PS17 |
| Cry5Ab1 | AAA67693 | | | Narva et al | 1991 | Bt darmstadiensis PS17 |
| Cry5Acl | 134543 | | | Payne et al | 1997 | |
| Cry5Ad1 | ABQ82087 | | | Lenane et al | 2007 | Bt L366 |
| Cry5Ba1 | AAA68598 | | | Foncerrada & Narva | 1997 | Bt PS86Q3 |
| Cry5Ba2 | ABW88931 | | | Guo et al | 2008 | YBT 1518 |
| Cry5Ba3 | AFJ04417 | 386277681 | 386277680 | Wang et al | 2012 | Bt zjfc85 |
| Cry5Ca1 | HM461869 | | 328833584 | Sun et al | 2010 | Sbt003 |
| Cry5Ca2 | ZP_04123426 | 228961871 | | Read et al | 2010 | Bt T13001 |
| Cry5Da1 | HM461870 | | 328833586 | Sun et al | 2010 | Sbt003 |
| Cry5Da2 | ZP_04123980 | 228962686 | | Read et al | 2010 | Bt T13001 |
| Cry5Ea1 | HM485580 | | 339186758 | Sun et al | 2010 | Sbt003 |
| Cry5Ea2 | ZP_04124038 | 228962776 | | Read et al | 2010 | Bt T13001 |
| Cry6Aa1 | AAA22357 | | | Narva et al | 1993 | Bt PS52A1 |
| Cry6Aa2 | AAM46849 | | | Bai et al | 2001 | YBT 1518 |
| Cry6Aa3 | ABH03377 | | | Jia et al | 2006 | Bt 96418 |
| Cry6Ba1 | AAA22358 | | | Narva et al | 1991 | Bt PS69D1 |
| Cry7Aa1 | AAA22351 | | | Lambert et al | 1992 | Bt galleriae PGSI245 |
| Cry7Ab1 | AAA21120 | | | Narva & Fu | 1994 | Bt dakota HD511 |
| Cry7Ab2 | AAA21121 | | | Narva & Fu | 1994 | Bt kumamotoensis 867 |
| Cry7Ab3 | ABX24522 | | | Song et al | 2008 | Bt WZ-9 |

TABLE 1-continued

Exemplary Target Gene and Polynucleotides

| Name | Acc No. | NCBI Protein | NCBI Nuc | Authors | Year | Source Strain |
|---|---|---|---|---|---|---|
| Cry7Ab4 | EU380678 | 170877973 | | Deng et al | 2011 | Bt HQ122 |
| Cry7Ab5 | ABX79555 | | | Aguirre-Arzola et al | 2008 | Bt monterrey GM-33 |
| Cry7Ab6 | ACI44005 | | | Deng et al | 2008 | Bt HQ122 |
| Cry7Ab7 | ADB89216 | | | Wang et al | 2010 | Bt GW6 |
| Cry7Ab8 | GU145299 | | | Feng & Guo | 2009 | |
| Cry7Ab9 | ADD92572 | | | Li et al | 2010 | Bt QG-121 |
| Cry7Ba1 | ABB70817 | | | Zhang et al | 2006 | Bt huazhongensis |
| Cry7Bb1 | KC156653 | | | Sampson et al | 2012 | |
| Cry7Ca1 | ABR67863 | | | Gao et al | 2007 | Bt BTH-13 |
| Cry7Cb1 | KC156698 | | | Sampson et al | 2012 | |
| Cry7Da1 | ACQ99547 | | | Yi et al | 2009 | Bt LH-2 |
| Cry7Da2 | HM572236 | | 328751616 | Shu et al | 2010 | |
| Cry7Da3 | KC156679 | | | Sampson et al | 2012 | |
| Cry7Ea1 | HM035086 | | 327505546 | Ming Sun et al | 2010 | Sbt009 |
| Cry7Ea2 | HM132124 | | 327359579 | Shu et al | 2010 | |
| Cry7Ea3 | EEM19403 | | | Read et al | 2010 | BGSC 4Y1 |
| Cry7Fa1 | HM035088 | | 327505550 | Ming Sun et al | 2010 | SBt009 |
| Cry7Fa2 | EEM19090 | | | Read et al | 2010 | BGSC 4Y1 |
| Cry7Fb1 | HM572235 | | 328751614 | Shu et al | 2010 | Bt |
| Cry7Fb2 | KC156682 | | | Sampson et al | 2012 | |
| Cry7Ga1 | HM572237 | | 328751618 | Shu et al | 2010 | Bt |
| Cry7Ga2 | KC156669 | | | Sampson et al | 2012 | |
| Cry7Gb1 | KC156650 | | | Sampson et al | 2012 | |
| Cry7Gc1 | KC156654 | | | Sampson et al | 2012 | |
| Cry7Gd1 | KC156697 | | | Sampson et al | 2012 | |
| Cry7Ha1 | KC156651 | | | Sampson et al | 2012 | |
| Cry7Ia1 | KC156665 | | | Sampson et al | 2012 | |
| Cry7Ja1 | KC156671 | | | Sampson et al | 2012 | |
| Cry7Ka1 | KC156680 | | | Sampson et al | 2012 | |
| Cry7Kb1 | BAM99306 | | | Takebe & Azuma | 2013 | Bt dakota |
| Cry7La1 | BAM99307 | | | Takebe & Azuma | 2013 | Bt dakota |
| Cry8Aa1 | AAA21117 | | | Narva & Fu | 1992 | Bt kumamotoensis |
| Cry8Ab1 | EU044830 | | | Cheng et al | 2007 | Bt B-JJX |
| Cry8Ac1 | KC156662 | | | Sampson et al | 2012 | |
| Cry8Ad1 | KC156684 | | | Sampson et al | 2012 | |
| Cry8Ba1 | AAA21118 | | | Narva & Fu | 1993 | Bt kumamotoensis |
| Cry8Bb1 | CAD57542 | | | Abad et al | 2002 | |
| Cry8Bc1 | CAD57543 | | | Abad et al | 2002 | |
| Cry8Ca1 | AAA21119 | | | Sato et al. | 1995 | Bt japonensis Buibui |
| Cry8Ca2 | AAR98783 | | | Shu et al | 2004 | Bt HBF-1 |
| Cry8Ca3 | EU625349 | 194272339 | 194272338 | Du et al | 2011 | Bt FTL-23 |
| Cry8Ca4 | ADB54826 | | | Li et al | 2010 | Bt S185 |
| Cry8Da1 | BAC07226 | | | Asano et al | 2002 | Bt galleriae |
| Cry8Da2 | BD133574 | | | Asano et al | 2002 | Bt |
| Cry8Da3 | BD133575 | | | Asano et al | 2002 | Bt |
| Cry8Db1 | BAF93483 | | | Yamaguchi et al | 2007 | Bt BBT2-5 |
| Cry8Ea1 | AAQ73470 | | | Fuping et al | 2003 | Bt 185 |
| Cry8Ea2 | EU047597 | | | Liu et al | 2007 | Bt B-DLL |
| Cry8Ea3 | KC855216 | | | Wei Wang | 2013 | |
| Cry8Fa1 | AAT48690 | | | Shu et al | 2004 | Bt 185 |
| Cry8Fa2 | HQ174208 | 307697880 | | Zang et al | 2010 | Bt DLL |
| Cry8Fa3 | AFH78109 | | | Su et al | 2012 | Bt L-27 |
| Cry8Ga1 | AAT46073 | | | Shu et al | 2004 | Bt HBF-18 |
| Cry8Ga2 | ABC42043 | | | Yan et al | 2008 | Bt 145 |
| Cry8Ga3 | FJ198072 | | | Sun et al | 2010 | Bt FCD114 |
| Cry8Ha1 | AAW81032 | | | Fuping et al | 2011 | Bt 185 |
| Cry8Ia1 | EU381044 | 170317962 | 170317961 | Yan et al | 2008 | Bt su4 |
| Cry8Ia2 | GU073381 | | 309274395 | Lixin Du et al | 2012 | Bt HW-11 |
| Cry8Ia3 | HM044664 | | 328833556 | Ming Sun | 2010 | |
| Cry8Ia4 | KC156674 | | | Sampson et al | 2012 | |
| Cry8Ib1 | GU325772 | | 314998609 | Ming Sun | 2012 | Bt F4 |
| Cry8Ib2 | KC156677 | | | Sampson et al | 2012 | |
| Cry8Ja1 | EU625348 | 194272337 | 194272336 | Du et al | 2011 | Bt FPT-2 |
| Cry8Ka1 | FJ422558 | 237506871 | 237506870 | Oliveira et al | 2011 | |
| Cry8Ka2 | ACN87262 | | | Noguera & Ibarra | 2009 | Bt kenyae |
| Cry8Kb1 | HM123758 | | 310616446 | Jun Zhu et al | 2010 | ST8 |
| Cry8Kb2 | KC156675 | | | Sampson et al | 2012 | |
| Cry8La1 | GU325771 | 314998608 | 314998607 | Ming Sun et al | 2012 | Bt F4 |
| Cry8Ma1 | HM044665 | | 328833558 | Ming Sun et al | 2010 | Sbt016 |
| Cry8Ma2 | EEM86551 | | | Read et al | 2010 | BGSC 4CC1 |
| Cry8Ma3 | HM210574 | | 305430488 | Jieyu Mao | 2010 | |
| Cry8Na1 | HM640939 | 302141260 | 302141259 | Li et al | 2011 | BtQ52-7 |
| Cry8Pa1 | HQ388415 | | 319769150 | Qiao Li | 2010 | Bt ST8 |
| Cry8Qa1 | HQ441166 | | 321266472 | Hongxia Liang | 2010 | Bt ST8 |
| Cry8Qa2 | KC152468 | | | Amadio et al | 2012 | Bt INTA Fr7-4 |

TABLE 1-continued

Exemplary Target Gene and Polynucleotides

| Name | Acc No. | NCBI Protein | NCBI Nuc | Authors | Year | Source Strain |
|---|---|---|---|---|---|---|
| Cry8Ra1 | AFP87548 | 400653691 | | Ben-Dov et al | 2012 | Bt R36 |
| Cry8Sa1 | JQ740599 | | | Singaravelu et al | 2012 | Bt Strain 62 |
| Cry8Ta1 | KC156673 | | | Sampson et al | 2012 | |
| Cry8-like | FJ770571 | | | Noguera & Ibarra | 2009 | Bt canadensis |
| Cry8-like | ABS53003 | | | Mangena et al | 2007 | Bt |
| Cry9Aa1 | CAA41122 | | | Shevelev et al | 1991 | Bt galleriae |
| Cry9Aa2 | CAA41425 | | | Gleave et al | 1992 | Bt DSIR517 |
| Cry9Aa3 | GQ249293 | | 293652149 | Su et al | 2012 | Bt SC5(D2) |
| Cry9Aa4 | GQ249294 | | 293652151 | Su et al | 2012 | Bt TO3C001 |
| Cry9Aa5 | JX174110 | | | Naimov et al | 2012 | |
| Cry9Aa-like | AAQ52376 | | | Baum et al | 2003 | |
| Cry9Ba1 | CAA52927 | | | Shevelev et al | 1993 | Bt galleriae |
| Cry9Ba2 | GU299522 | | | Zhao et al | 2010 | Bt B-SC5 |
| Cry9Bb1 | AAV28716 | | | Silva-Werneck et al | 2004 | Bt japonensis |
| Cry9Ca1 | CAA85764 | | | Lambert et al | 1996 | Bt tolworthi |
| Cry9Ca2 | AAQ52375 | | | Baum et al | 2003 | |
| Cry9Da1 | BAA19948 | | | Asano | 1997 | Bt japonensis N141 |
| Cry9Da2 | AAB97923 | | | Wasano & Ohba | 1998 | Bt japonensis |
| Cry9Da3 | GQ249293 | | 293652153 | Su et al | 2012 | Bt SC5 (D2) |
| Cry9Da4 | GQ249297 | | 293652157 | Su et al | 2012 | Bt TO3B001 |
| Cry9Db1 | AAX78439 | | | Flannagan & Abad | 2005 | Bt kurstaki DP1019 |
| Cry9Dc1 | KC156683 | | | Sampson et al | 2012 | |
| Cry9Ea1 | BAA34908 | | | Midoh & Oyama | 1998 | Bt aizawai SSK-10 |
| Cry9Ea2 | AA012908 | | | Li et al | 2001 | Bt B-Hm-16 |
| Cry9Ea3 | ABM21765 | | | Lin et al | 2006 | Bt lyA |
| Cry9Ea4 | ACE88267 | | | Zhu et al | 2008 | Bt ywc5-4 |
| Cry9Ea5 | ACF04743 | | | Zhu et al | 2008 | Bts |
| Cry9Ea6 | ACG63872 | | | Liu & Guo | 2008 | Bt 11 |
| Cry9Ea7 | FJ380927 | | | Sun et al | 2009 | Bt 4 |
| Cry9Ea8 | GQ249292 | | 293652147 | Su et al | 2012 | Bt SC5(E8) |
| Cry9Ea9 | JN651495 | | | Li Yuhong | 2011 | Bt LTS-7 |
| Cry9Eb1 | CAC50780 | | | Arnaut et al | 2001 | |
| Cry9Eb2 | GQ249298 | | 293652159 | Su et al | 2012 | Bt T23001 |
| Cry9Eb3 | KC156646 | | | Sampson et al | 2012 | |
| Cry9Ec1 | AAC63366 | | | Wasano et al | 2003 | Bt galleriae |
| Cry9Ed1 | AAX78440 | | | Flannagan & Abad | 2005 | Bt kurstaki DP1019 |
| Cry9Ee1 | GQ249296 | | 293652155 | Su et al | 2009 | Bt TO3B001 |
| Cry9Ee2 | KC156664 | | | Sampson et al | 2012 | |
| Cry9Fa1 | KC156692 | | | Sampson et al | 2012 | |
| Cry9Gal | KC156699 | | | Sampson et al | 2012 | |
| Cry9-like | AAC63366 | | | Wasano et al | 1998 | Bt galleriae |
| Cry1OAa1 | AAA22614 | | | Thorne et al | 1986 | Bt israelensis |
| Cry10Aa2 | E00614 | | | Aran & Toomasu | 1996 | Bt israelensis ONR-60A |
| Cry10Aa3 | CAD30098 | | | Berry et al | 2002 | Bt israelensis |
| Cry10Aa4 | AFB18318 | | | Li et al | 2012 | Bti BRC-LLP29 |
| Cry1OA-like | DQ167578 | | | Mahalakshmi et al | 2006 | Bt LDC-9 |
| Cry1lAa1 | AAA22352 | | | Donovan et al | 1988 | Bt israelensis |
| Cry1lAa2 | AAA22611 | | | Adams et al | 1989 | Bt israelensis |
| Cry1lAa3 | CAD30081 | | | Berry et al | 2002 | Bt israelensis |
| Cry1lAa4 | AFB18319 | | | Li et al | 2012 | Bti BRC-LLP29 |
| Cry1lAa-like | DQ166531 | | | Mahalakshmi et al | 2007 | Bt LDC-9 |
| Cry11Ba1 | CAA60504 | | | Delecluse et al | 1995 | Bt jegathesan 367 |
| Cry11Bb1 | AAC97162 | | | Orduz et al | 1998 | Bt medellin |
| Cry11Bb2 | HM068615 | | | Melnikov et al | 2010 | Bt K34 |
| Cry12Aa1 | AAA22355 | | | Narva et al | 1991 | Bt PS33F2 |
| Cry13Aa1 | AAA22356 | | | Narva et al | 1992 | Bt PS63B |
| Cry14Aa1 | AAA21516 | | | Narva et al | 1994 | Bt sotto PS80JJ1 |
| Cry14Ab1 | KC156652 | | | Sampson et al | 2012 | |
| Cry15Aa1 | AAA22333 | | | Brown & Whiteley | 1992 | Bt thompsoni |
| Cry16Aa1 | CAA63860 | | | Barloy et al | 1996 | Cb malaysia CH18 |
| Cry17Aa1 | CAA67841 | | | Barloy et al | 1998 | Cb malaysia CH18 |
| Cry18Aa1 | CAA67506 | | | Zhang et al | 1997 | Paenibacillus popilliae |
| Cry18Ba1 | AAF89667 | | | Patel et al | 1999 | Paenibacillus popilliae |
| Cry18Ca1 | AAF89668 | | | Patel et al | 1999 | Paenibacillus popilliae |
| Cry19Aa1 | CAA68875 | | | Rosso & Delecluse | 1996 | Bt jegathesan 367 |
| Cry19Ba 1 | BAA32397 | | | Hwang et al | 1998 | Bt higo |
| Cry19Ca1 | AFM37572 | | | Soufiane & Cote | 2012 | BGSC 4CE1 |
| Cry20Aa1 | AAB 93476 | | | Lee & Gill | 1997 | Bt fukuokaensis |
| Cry20Ba1 | ACS93601 | | | Noguera & Ibarra | 2009 | Bt higo LBIT-976 |
| Cry20Ba2 | KC156694 | | | Sampson et al | 2012 | |
| Cry20-like | GQ144333 | | | Yi et al | 2009 | Bt Y-5 |
| Cry21Aa1 | 132932 | | | Payne et al | 1996 | |

TABLE 1-continued

Exemplary Target Gene and Polynucleotides

| Name | Acc No. | NCBI Protein | NCBI Nuc | Authors | Year | Source Strain |
|---|---|---|---|---|---|---|
| Cry21Aa2 | 166477 | | | Feitelson | 1997 | |
| Cry21Ba1 | BAC06484 | | | Sato & Asano | 2002 | Bt roskildiensis |
| Cry21Ca1 | JF521577 | | | Liu et al | 2013 | |
| Cry21Ca2 | KC156687 | | | Sampson et al | 2012 | |
| Cry21Da1 | JF521578 | | | Liu et al | 2011 | Sbt072 |
| Cry21Ea1 | KC865049 | | | Ming Sun | 2013 | |
| Cry21Fa1 | KF701307 | | | Iatsenko et al | 2013 | |
| Cry21Ga1 | KF771885 | | | Iatsenko et al | 2013 | |
| Cry21Ha1 | KF771886 | | | Iatsenko et al | 2013 | |
| Cry22Aa1 | 134547 | | | Payne et al | 1997 | |
| Cry22Aa2 | CAD43579 | | | Isaac et al | 2002 | Bt |
| Cry22Aa3 | ACD93211 | | | Du et al | 2008 | Bt FZ-4 |
| Cry22Ab1 | AAK50456 | | | Baum et al | 2000 | Bt EG4140 |
| Cry22Ab2 | CAD43577 | | | Isaac et al | 2002 | Bt |
| Cry22Ba1 | CAD43578 | | | Isaac et al | 2002 | Bt |
| Cry22Bb1 | KC156672 | | | Sampson et al | 2012 | |
| Cry23Aa1 | AAF76375 | | | Donovan et al | 2000 | Bt |
| Cry24Aa1 | AAC61891 | | | Kawalek and Gill | 1998 | Bt jegathesan |
| Cry24Ba1 | BAD32657 | | | Ohgushi et al | 2004 | Bt sotto |
| Cry24Ca1 | CAJ43600 | | | Beron & Salerno | 2005 | Bt FCC-41 |
| Cry25Aa1 | AAC61892 | | | Kawalek and Gill | 1998 | Bt jegathesan |
| Cry26Aa1 | AAD25075 | | | Wojciechowska et al | 1999 | Bt finitimus B-1166 |
| Cry27Aa1 | BAA82796 | | | Saitoh | 1999 | Bt higo |
| Cry28Aa1 | AAD24189 | | | Wojciechowska et al | 1999 | Bt finitimus B-1161 |
| Cry28Aa2 | AAG00235 | | | Moore and Debro | 2000 | Bt finitimus |
| Cry29Aa1 | CAC80985 | | | Delecluse et al | 2000 | Bt medellin |
| Cry29Ba1 | KC865046 | | | Ming Sun | 2013 | |
| Cry30Aa1 | CAC80986 | | | Delecluse et al | 2000 | Bt medellin |
| Cry30Ba1 | BAD00052 | | | Ito et al | 2003 | Bt entomocidus |
| Cry30Ca1 | BAD67157 | | | Ohgushi et al | 2004 | Bt sotto |
| Cry30Ca2 | ACU24781 | | | Sun and Park | 2009 | Bt jegathesan 367 |
| Cry30Da1 | EF095955 | | | Shu et al | 2006 | Bt Y41 |
| Cry30Db1 | BAE80088 | | | Kishida et al | 2006 | Bt aizawai BUN1-14 |
| Cry30Ea1 | ACC95445 | | | Fang et al | 2007 | Bt S2160-1 |
| Cry30Ea2 | FJ499389 | 237688240 | 237688239 | Zhu et al | 2011 | Bt Ywc2-8 |
| Cry30Fa1 | ACI22625 | | | Tan et al | 2008 | Bt MC28 |
| Cry30Ga1 | ACG60020 | | | Zhu et al | 2008 | Bt HS18-1 |
| Cry30Ga2 | HQ638217 | 320383831 | 320383830 | Tian et al | 2010 | Bt S2160-1 |
| Cry31Aa1 | BAB11757 | | | Saitoh & Mizuki | 2000 | Bt 84-HS-1-11 |
| Cry31Aa2 | AAL87458 | | | Jung and Cote | 2000 | Bt M15 |
| Cry31Aa3 | BAE79808 | | | Uemori et al | 2006 | Bt B0195 |
| Cry31Aa4 | BAF32571 | | | Yasutake et al | 2006 | Bt 79-25 |
| Cry31Aa5 | BAF32572 | | | Yasutake et al | 2006 | Bt 92-10 |
| Cry31Aa6 | BAI44026 | | | Nagamatsu et al | 2010 | M019 |
| Cry31Ab1 | B AE79809 | | | Uemori et al | 2006 | Bt B0195 |
| Cry31Ab2 | BAF32570 | | | Yasutake et al | 2006 | Bt 31-5 |
| Cry31Ac1 | BAF34368 | | | Yasutake et al | 2006 | Bt 87-29 |
| Cry31Ac2 | AB731600 | | | Hayakawa et al | 2012 | Bt B0462 |
| Cry31Ad1 | BAI44022 | | | Nagamatsu et al | 2010 | Bt M019 |
| Cry32Aa1 | AAG36711 | | | Balasubramanian et al | 2001 | Bt yunnanensis |
| Cry32Aa2 | GU063849 | | 308445182 | Lixin Du et al | 2012 | Bt FBG-1 |
| Cry32Ab1 | GU063850 | | 308445184 | Lixin Du et al | 2012 | Bt FZ-2 |
| Cry32Ba1 | BAB78601 | | | Takebe et al | 2001 | Bt |
| Cry32Ca1 | BAB78602 | | | Takebe et al | 2001 | Bt |
| Cry32Cb1 | KC156708 | | | Sampson et al | 2012 | |
| Cry32Da1 | BAB78603 | | | Takebe et al | 2001 | Bt |
| Cry32Ea1 | GU324274 | | 301299156 | Lixin Du | 2010 | Bt |
| Cry32Ea2 | KC156686 | | | Sampson et al | 2012 | |
| Cry32Eb1 | KC156663 | | | Sampson et al | 2012 | |
| Cry32Fa1 | KC156656 | | | Sampson et al | 2012 | |
| Cry32Ga1 | KC156657 | | | Sampson et al | 2012 | |
| Cry32Ha1 | KC156661 | | | Sampson et al | 2012 | |
| Cry32Hb1 | KC156666 | | | Sampson et al | 2012 | |
| Cry32Ia1 | KC156667 | | | Sampson et al | 2012 | |
| Cry32Ja1 | KC156685 | | | Sampson et al | 2012 | |
| Cry32Ka1 | KC156688 | | | Sampson et al | 2012 | |
| Cry32La1 | KC156689 | | | Sampson et al | 2012 | |
| Cry32Ma1 | KC156690 | | | Sampson et al | 2012 | |
| Cry32Mb1 | KC156704 | | | Sampson et al | 2012 | |
| Cry32Na1 | KC156691 | | | Sampson et al | 2012 | |
| Cry32Oa1 | KC156703 | | | Sampson et al | 2012 | |
| Cry32Pa1 | KC156705 | | | Sampson et al | 2012 | |
| Cry32Qa1 | KC156706 | | | Sampson et al | 2012 | |
| Cry32Ra1 | KC156707 | | | Sampson et al | 2012 | |
| Cry32Sa1 | KC156709 | | | Sampson et al | 2012 | |

TABLE 1-continued

Exemplary Target Gene and Polynucleotides

| Name | Acc No. | NCBI Protein | NCBI Nuc | Authors | Year | Source Strain |
|---|---|---|---|---|---|---|
| Cry32Ta1 | KC156710 | | | Sampson et al | 2012 | |
| Cry32Ua1 | KC156655 | | | Sampson et al | 2012 | |
| Cry33Aa1 | AAL26871 | | | Kim et al | 2001 | Bt dakota |
| Cry34Aa1 | AAG50341 | | | Ellis et al | 2001 | Bt PS80JJ1 |
| Cry34Aa2 | AAK64560 | | | Rupar et al | 2001 | Bt EG5899 |
| Cry34Aa3 | AAT29032 | | | Schnepf et al | 2004 | Bt PS69Q |
| Cry34Aa4 | AAT29030 | | | Schnepf et al | 2004 | Bt PS185GG |
| Cry34Ab1 | AAG41671 | | | Moellenbeck et al | 2001 | Bt PS149B 1 |
| Cry34Ac1 | AAG50118 | | | Ellis et al | 2001 | Bt PS167H2 |
| Cry34Ac2 | AAK64562 | | | Rupar et al | 2001 | Bt EG9444 |
| Cry34Ac3 | AAT29029 | | | Schnepf et al | 2004 | Bt KR1369 |
| Cry34B a 1 | AAK64565 | | | Rupar et al | 2001 | Bt EG4851 |
| Cry34Ba2 | AAT29033 | | | Schnepf et al | 2004 | Bt PS201L3 |
| Cry34Ba3 | AAT29031 | | | Schnepf et al | 2004 | Bt PS201HH2 |
| Cry35Aa1 | AAG50342 | | | Ellis et al | 2001 | Bt PS80JJ1 |
| Cry35Aa2 | AAK64561 | | | Rupar et al | 2001 | Bt EG5899 |
| Cry35Aa3 | AAT29028 | | | Schnepf et al | 2004 | Bt PS69Q |
| Cry35Aa4 | AAT29025 | | | Schnepf et al | 2004 | Bt PS185GG |
| Cry35Ab1 | AAG41672 | | | Moellenbeck et al | 2001 | Bt PS149B1 |
| Cry35Ab2 | AAK64563 | | | Rupar et al | 2001 | Bt EG9444 |
| Cry35Ab3 | AY536891 | | | AAT29024 | 2004 | Bt KR1369 |
| Cry35Ac1 | AAG50117 | | | Ellis et al | 2001 | Bt PS167H2 |
| Cry35Ba1 | AAK64566 | | | Rupar et al | 2001 | Bt EG4851 |
| Cry35Ba2 | AAT29027 | | | Schnepf et al | 2004 | Bt PS201L3 |
| Cry35Ba3 | AAT29026 | | | Schnepf et al | 2004 | Bt PS201HH2 |
| Cry36Aa1 | AAK64558 | | | Rupar et al | 2001 | Bt |
| Cry37Aa1 | AAF76376 | | | Donovan et al | 2000 | Bt |
| Cry38Aa1 | AAK64559 | | | Rupar et al | 2000 | Bt |
| Cry39Aa1 | BAB72016 | | | Ito et al | 2001 | Bt aizawai |
| Cry40Aa1 | BAB72018 | | | Ito et al | 2001 | Bt aizawai |
| Cry4OB a1 | BAC77648 | | | Ito et al | 2003 | Bunl-14 |
| Cry40Ca1 | EU381045 | 170317964 | 170317963 | Shu et al | 2011 | Bt Y41 |
| Cry40Da1 | ACF15199 | | | Zhang et al | 2008 | Bt S2096-2 |
| Cry4lAa1 | BAD35157 | | | Yamashita et al | 2003 | Bt A1462 |
| Cry4lAb1 | BAD35163 | | | Yamashita et al | 2003 | Bt A1462 |
| Cry41Ba1 | HM461871 | | 328833588 | Sun et al | 2010 | Sbt021 |
| Cry41Ba2 | ZP_04099652 | 228936898 | | Read et al | 2010 | BGSC 4AW1 |
| Cry42Aa1 | BAD35166 | | | Yamashita et al | 2003 | Bt A1462 |
| Cry43Aa1 | BAD15301 | | | Yokoyama and Tanaka | 2003 | P. lentimorbus semadara |
| Cry43Aa2 | BAD95474 | | | Nozawa | 2004 | P. popilliae popilliae |
| Cry43Ba1 | BAD15303 | | | Yokoyama and Tanaka | 2003 | P. lentimorbus semadara |
| Cry43Ca1 | KC156676 | | | Sampson et al | 2012 | |
| Cry43Cb1 | KC156695 | | | Sampson et al | 2012 | |
| Cry43Cc1 | KC156696 | | | Sampson et al | 2012 | |
| Cry43-like | BAD15305 | | | Yokoyama and Tanaka | 2003 | P. lentimorbus semadara |
| Cry44Aa | BAD08532 | | | Ito et al | 2004 | Bt entomocidus INA288 |
| Cry45Aa | BAD22577 | | | Okumura et al | 2004 | Bt 89-T-34-22 |
| Cry46Aa | BAC79010 | | | Ito et al | 2004 | Bt dakota |
| Cry46Aa2 | BAG68906 | | | Ishikawa et al | 2008 | Bt A1470 |
| Cry46Ab | BAD35170 | | | Yamagiwa et al | 2004 | Bt |
| Cry47Aa | AAY24695 | | | Kongsuwan et al | 2005 | Bt CAA890 |
| Cry48Aa | CAJ18351 | | | Jones and Berry | 2005 | Bs IAB59 |
| Cry48Aa2 | CAJ86545 | | | Jones and Berry | 2006 | Bs 47-6B |
| Cry48Aa3 | CAJ86546 | | | Jones and Berry | 2006 | Bs NHA15b |
| Cry48Ab | CAJ86548 | | | Jones and Berry | 2006 | Bs LP1G |
| Cry48Ab2 | CAJ86549 | | | Jones and Berry | 2006 | Bs 2173 |
| Cry49Aa | CAH56541 | | | Jones and Berry | 2005 | Bs IAB59 |
| Cry49Aa2 | CAJ86541 | | | Jones and Berry | 2006 | Bs 47-6B |
| Cry49Aa3 | CAJ86543 | | | Jones and Berry | 2006 | BsNHA15b |
| Cry49Aa4 | CAJ86544 | | | Jones and Berry | 2006 | Bs 2173 |
| Cry49Ab1 | CAJ86542 | | | Jones and Berry | 2006 | Bs LP1G |
| Cry50Aa1 | BAE86999 | 89885725 | 89885724 | Ohgushi et al | 2006 | Bt sotto |
| Cry5OBa1 | GU446675 | | | Zhang & Fang | 2011 | Bt S2160-1 |
| Cry5OBa2 | GU446676 | | | Zhang et al | 2011 | Bt S3161-3 |
| Cry5lAa1 | AB 114444 | 112253719 | 112253718 | Meng et al | 2006 | Bt F14-1 |
| Cry5lAa2 | GU570697 | | | Baum et al | 2011 | EG2934 |
| Cry52Aa1 | EF613489 | | | Shu et al | 2010 | Bt Y41 |
| Cry52B a1 | FJ361760 | 227976386 | 227976385 | Zhu et al | 2010 | Bt BM59-2 |
| Cry53Aa1 | EF633476 | | | Shu et al | 2010 | Bt Y41 |
| Cry53Ab1 | FJ361759 | 227976384 | 227976383 | Zhu et al | 2011 | Bt MC28 |
| Cry54Aa1 | ACA52194 | 169261091 | 169261090 | Tan et al | 2009 | Bt MC28 |
| Cry54Aa2 | GQ140349 | | 291010566 | Lixin Du et al | 2012 | Bt FBG25 |

TABLE 1-continued

Exemplary Target Gene and Polynucleotides

| Name | Acc No. | NCBI Protein | NCBI Nuc | Authors | Year | Source Strain |
|---|---|---|---|---|---|---|
| Cry54Ab1 | JQ916908 | | | Guan Peng | 2012 | Bt MC28 |
| Cry54B a1 | GU446677 | | | Zhang & Fang | 2010 | Bt S2160-1 |
| Cry55Aa1 | ABW88932 | | | Guo et al | 2008 | YBT 1518 |
| Cry55Aa2 | AAE33526 | 10056620 | | Bradfisch et al | 2000 | Bt Y41 |
| Cry55Aa3 | HG764207 | | | Balasubramani et al | 2013 | Bt T44 |
| Cry56Aa1 | ACU57499 | 256033941 | 256033940 | Zhu et al | 2010 | Bt Ywc2-8 |
| Cry56Aa2 | GQ483512 | 300837105 | 300837104 | Guan et al | 2009 | Bt G7-1 |
| Cry56Aa3 | JX025567 | | | Qiao Li et al | 2012 | Bt HS18-1 |
| Cry57Aa1 | ANC87261 | 225348555 | 225348554 | Noguera & Ibarra | 2009 | Bt kim |
| Cry57Ab1 | KF638650 | | | Guowang Zhou | 2013 | |
| Cry58Aa1 | ANC87260 | 225348553 | 225348552 | Noguera & Ibarra | 2009 | Bt entomocidus |
| Cry59B a1 | JN790647 | | | Qiao Li et al | 2012 | Bt Bm59-2 |
| Cry59Aa1 | ACR43758 | 239638225 | 239638224 | Noguera & Ibarra | 2009 | Bt kim LBIT-980 |
| Cry60Aa1 | ACU24782 | 255653180 | 255653179 | Sun and Park | 2009 | Bt jegathesan |
| Cry60Aa2 | EA057254 | 74494162 | 74494143 | Anderson et al | 2005 | Bt israelensis |
| Cry60Aa3 | EEM99278 | 228854669 | 228854666 | Read et al | 2009 | Bt IBL 4222 |
| Cry60Ba1 | GU810818 | 292398077 | 292398076 | Sun and Park | 2009 | Bt malayensis |
| Cry60Ba2 | EAO57253 | | | Anderson et al | 2005 | Bt israelensis |
| Cry60Ba3 | EEM99279 | | | Read et al | 2009 | Bt IBL 4222 |
| Cry6lAa1 | HM035087 | | 327505548 | Ming Sun et al | 2010 | Sbt009 |
| Cry6lAa2 | HM132125 | | 327359581 | Shu et al | 2010 | |
| Cry6lAa3 | EEM19308 | 228770790 | 228770789 | Read et al | 2010 | BGSC 4Y1 |
| Cry62Aa1 | HM054509 | | 302753235 | Jun Zhu et al | 2010 | ST7 |
| Cry63Aa1 | BAI44028 | 260268375 | | Nagamatsu et al | 2010 | M019 |
| Cry64Aa1 | BAJ05397 | 294661779 | | Ekino et al | 2010 | Bt tohokuensis |
| Cry65Aa1 | HM461868 | | 328833581 | Sun et al | 2010 | SBt 003 |
| Cry65Aa2 | ZP_04123838 | 228962456 | | Read et al | 2010 | T13001 |
| Cry66Aa1 | HM485581 | | 339186760 | Sun et al | 2010 | SBt 021 |
| Cry66Aa2 | ZP_04099945 | 228937265 | | Read et al | 2010 | BGSC 4AW1 |
| Cry67Aa1 | HM485582 | | 339186762 | Sun et al | 2010 | SBt 009 |
| Cry67Aa2 | ZP_04148882 | 228988817 | | Read et al | 2010 | BGSC 4Y1 |
| Cry68Aa1 | HQ113114 | | 327446752 | Peng Guan et al | 2012 | Bt MC28 |
| Cry69Aa1 | HQ401006 | | 332139130 | Peng Guan | 2011 | Bt MC28 |
| Cry69Aa2 | JQ821388 | | | Peng Guan | 2012 | Bt MC28 |
| Cry69Ab1 | JN209957 | | | Yujie Tang | 2011 | Bt hs18-1 |
| Cry70Aa1 | JN646781 | | | Qiao Li | 2011 | Bt hs18-1 |
| Cry70Ba1 | AD051070 | 308756031 | | Guan et al | 2011 | Bt MC28 |
| Cry70Bb1 | EEL67276 | 228715456 | | Read et al | 2009 | Bc AH603 |
| Cry7lAa1 | JX025568 | | | Qiao Li et al | 2012 | Bt Hs18-1 |
| Cry72Aa1 | JX025569 | | | Qiao Li et al | 2012 | Bt Hs18-1 |
| CytlAa1 | X03182 | | | Waalwijk et al | 1985 | Bt israelensis |
| CytlAa2 | X04338 | | | Ward & Ellar | 1986 | Bt israelensis |
| CytlAa3 | Y00135 | | | Earp & Ellar | 1987 | Bt morrisoni PG14 |
| CytlAa4 | M35968 | | | Galjart et al | 1987 | Bt morrisoni PG14 |
| CytlAa5 | AL731825 | | | Berry et al | 2002 | Bt israelensis |
| CytlAa6 | ABC17640 | | | Zhang et al | 2005 | Bt LLP29 |
| CytlAa7 | KF152888 | | | Qinyang Hong | 2013 | Bt BRC-HQY1 |
| CytlAa-like | ABB01172 | | | Mahalakshmi | 2007 | Bt LDC-9 |
| Cyt1Ab1 | X98793 | | | Thiery et al | 1997 | Bt medellin |
| Cyt1Ba1 | U37196 | | | Payne et al | 1995 | Bt neoleoensis |
| CytlCa1 | AL731825 | | | Berry et al | 2002 | Bt israelensis |
| Cyt1Da1 | HQ113115 | | 317575156 | Peng Guan | 2012 | Bt MC28 |
| Cyt1Da2 | JN226105 | | 354551244 | Yujie Tang | 2011 | hs18-1 |
| Cyt2Aa1 | Z14147 | | | Koni & Ellar | 1993 | Bt kyushuensis |
| Cyt2Aa2 | AF472606 | | | Promdonkoy & Panyim | 2001 | Bt darmstadiensis73El 0 |
| Cyt2Aa3 | EU835185 | | | Zhu et al | 2008 | Bt MC28 |
| Cyt2Aa4 | AEG19547 | | | Guo et al | 2011 | Bt WFS-97 |
| Cyt2B a1 | U52043 | | | Guerchicoff et al | 1997 | Bt israelensis 4Q2 |
| Cyt2Ba2 | AF020789 | | | Guerchicoff et al | 1997 | Bt israelensis PG14 |
| Cyt2Ba3 | AF022884 | | | Guerchicoff et al | 1997 | Bt fuokukaensis |
| Cyt2Ba4 | AF022885 | | | Guerchicoff et al | 1997 | Bt morrisoni HD12 |
| Cyt2Ba5 | AF022886 | | | Guerchicoff et al | 1997 | Bt morrisoni HD518 |
| Cyt2Ba6 | AF034926 | | | Guerchicoff et al | 1997 | Bt tenebrionis |
| Cyt2Ba7 | AF215645 | | | Yu & Pang | 2000 | Bt T301 |
| Cyt2Ba8 | AF215646 | | | Yu & Pang | 2000 | Bt T36 |
| Cyt2Ba9 | AL731825 | | | Berry et al | 2002 | Bt israelensis |
| Cyt2Ba10 | ACX54358 | | | Sauka & Benintende | 2009 | Bti HD 567 |
| Cyt2Ba11 | ACX54359 | | | Sauka & Benintende | 2009 | Bti HD 522 |
| Cyt2Ba12 | ACX54360 | | | Sauka & Benintende | 2009 | Bti INTA H41-1 |
| Cyt2Ba13 | FJ205865 | 209168617 | | Sauka & Benintende | 2009 | INTA 160-2 |
| Cyt2Ba14 | FJ205866 | 209168619 | | Sauka & Benintende | 2009 | Bti IPS82 |
| Cyt2Ba15 | JF283552 | 342360662 | 342360661 | Zhang et al | 2011 | Bt LLP29 |
| Cyt2Ba-like | ABE99695 | | | Mahalakshmi et al | 2007 | Bt LDC-9 |
| Cyt2Bb1 | U82519 | | | Cheong & Gill | 1997 | Bt jegathesan |
| Cyt2Bc1 | CAC80987 | | | Delecluse et al | 1999 | Bt medellin |

TABLE 1-continued

Exemplary Target Gene and Polynucleotides

| Name | Acc No. | NCBI Protein | NCBI Nuc | Authors | Year | Source Strain |
|---|---|---|---|---|---|---|
| Cyt2B-like | DQ341380 | | | Zhang et al | 2005 | |
| Cyt2Ca1 | AAK50455 | | | Baum et al | 2001 | Bt |
| Cyt3Aa1 | HM596591 | | 305433345 | Zhu Jun | 2010 | Bt TD516 |

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The following examples are offered by way of illustration and not by way of limitation.

EXPERIMENTAL

Example 1

Sampling and DNA preparation: Soil samples were collected from 7 diverse environmental niches on private property in Apex, N.C. Genomic DNA was prepared from 400 mg of each sample with the NucleoSpin® Soil preparation kit from Clontech. Prior to DNA extraction, intact samples were preserved as glycerol stocks for future identification of the organism bearing genes of interest and for retrieval of complete gene sequences. Yields of DNA from soil samples ranged from 0.36 to 9.1 micrograms with A260/A280 ratios ranging from 1.50 to 1.89 (Table 2). Because soil DNA preparations have been reported to inhibit PCR reactions, which could hinder the gene enrichment protocol, DNA samples were used as template for PCR with primers designed against the microbial 16S rRNA. Samples 1-4 yielded a PCR product (Table 2), and those 4 samples were used for gene enrichment experiments. Additional DNA samples were prepared from pools of cultured environmental microbes containing up to 25,000 colonies. To enrich these microbial pools for organisms likely to contain genes of interest, samples collected from about 920 diverse environmental sources were either (1) pasteurized to select for spore formers before plating on 0.1×LB medium, or (2) plated on media that selects for gram-positive bacteria (such as, for example, Brilliance Bacillus cereus agar from Oxoid Microbiology Products). Soil DNA preparations were spiked with genomic DNA from 4 organisms known to contain genes of interest at various ratios to serve as positive controls for the process (Table 2).

TABLE 2

Environmental sources for DNA preparations with yields and spectrophotometric quality assessments.

| | Environmental Sample Description | DNA Yield (11 g) | A260/ A280 | A260/ A230 | PCR |
|---|---|---|---|---|---|
| 1 | Pond (Center) | 2.9 | 1.79 | 1.76 | Yes |
| 2 | Forest | 6.5 | 1.81 | 1.59 | Yes |
| 3 | Pond (Edge) | 0.36 | 1.50 | 1.28 | Yes |
| 4 | Garden | 6.9 | 1.86 | 1.62 | Yes |
| 5 | Peach orchid | 9.1 | 1.89 | 2.05 | No |
| 6 | Front yard | 9.1 | 1.64 | 1.04 | No |
| 7 | Broom sedge | 8.7 | 1.74 | 1.57 | No |
| 8 | 100 pooled colonies | | | | Yes |
| 9 | 1000 pooled colonies | | | | Yes |
| 10 | 10,000 pooled colonies | | | | Yes |
| 11 | 25,000 pooled colonies | | | | Yes |

TABLE 3

Experimental design for gene enrichment experiments:

| | # Microbes screened | Microbial DNA source | BT spike | Approx, copy #/gene |
|---|---|---|---|---|
| | | Positive control | | |
| 1 | 25 | BT only | 25 strains | 10,000,000 |
| | | Soil DNA spiked with BT DNA | | |
| 2 | ND | Soil 1-4 | 1/50,000,000 (60 fg) | 5 |
| 3 | ND | Soil 1-4 | 1/1,000,000 (3 pg) | 250 |
| 4 | ND | Soil 1-4 | 1/50,000 (60 pg) | 5,000 |
| 5 | ND | Soil 1-4 | 1/1000 (3 ng) | 250,000 |
| | | Colonies from pasteurized collections spiked with BT colonies before DNA preparation | | |
| 6 | 100 | Pasteurized collections | 1 colony each x4 (1/25) | 2,500,00 |
| 7 | 1000 | Pasteurized collections | 1 colony each x4 (1/250) | 250,000 |
| 8 | 10,000 | Pasteurized collections | 1 colony each x4 (1/2500) | 25,000 |
| 9 | 25,000 | Pasteurized collections | 1 colony each x4 (1/6250) | 10,000 |
| 10 | 10,000 | Pasteurized collections | 10 colonies each x4 (1/250) | 250,000 |
| 11 | 10,000 | Pasteurized collections | 100 colonies each x4 (1/25) | 2,500,000 |

Shown in Table 3 are the DNA inputs for capture reactions including the environmental sample (described in Table 2), genes used as positive controls and the representation of genomic DNA from the positive control strains as a ratio to total DNA input.

Oligonucleotide baits: Baits for gene capture consisted of approximately 30,000 biotinylated 120 base RNA oligonucleotides that were designed against approximately 900 genes and represent 9 distinct gene families of agricultural interest (Table 4). In addition to genes of interest, additional sequences were included as positive controls (housekeeping genes) and for microbe species identification (16S rRNA).

Starting points for baits were staggered at 60 bases to confer 2× coverage for each gene. Baits were synthesized at Agilent with the SureSelect® technology. However, additional products for similar use are available from Agilent and other vendors including NimbleGen® (SeqCap® EZ), Mycroarray (MYbaits®), Integrated DNA Technologies (XGen®), and LC Sciences (OligoMix®).

TABLE 4

Gene families queried in capture reactions with the number of genes queried for each family.

| Gene Family | # genes |
|---|---|
| Cry | 640 |
| Cyt | 7 |
| Mtx | 25 |
| Binary | 33 |
| Vip | 104 |
| Sip | 2 |
| Misc. toxins | 25 |
| EPSPS | 14 |
| HPPD | 22 |
| 16S | 373 |
| Housekeeping | 8 |
| TOTAL | 1253 |

TABLE 5

Example baits designed against Cry1Aa1.

| SEQ ID NO | Base pair range | Sequence |
|---|---|---|
| 1 | 1 . . . 120 | ATGGATAACAATCCGAACATCAATGAATGCATTCCTTATAATTGTTTAAGTAACCCTGAAGTAGAAGTATTAGGTGGAGAAAGAATAGAAACTGGTTACACCCCAATCGATATTTCCTTG |
| 2 | 61 . . . 180 | GTAGAAGTATTAGGTGGAGAAAGAATAGAAACTGGTTACACCCCAATCGATATTTCCTTGTCGCTAACGCAATTTCTTTTGAGTGAATTTGTTCCCGGTGCTGGATTTGTGTTAGGACTA |
| 3 | 121 . . . 240 | TCGCTAACGCAATTTCTTTTGAGTGAATTTGTTCCCGGTGCTGGATTTGTGTTAGGACTAGTTGATATAATATGGGGAATTTTTGGTCCCTCTCAATGGGACGCATTTCCTGTACAAATT |
| 4 | 181 . . . 300 | GTTGATATAATATGGGGAATTTTTGGTCCCTCTCAATGGGACGCATTTCCTGTACAAATTGAACAGTTAATTAACCAAAGAATAGAAGAATTCGCTAGGAACCAAGCCATTTCTAGATTA |
| 5 | 241 . . . 360 | GAACAGTTAATTAACCAAAGAATAGAAGAATTCGCTAGGAACCAAGCCATTTCTAGATTAGAAGGACTAAGCAATCTTTATCAAATTTACGCAGAATCTTTTAGAGAGTGGGAAGCAGAT |
| 6 | 301 . . . 420 | GAAGGACTAAGCAATCTTTATCAAATTTACGCAGAATCTTTTAGAGAGTGGGAAGCAGATCCTACTAATCCAGCATTAAGAGAAGAGATGCGTATTCAATTCAATGACATGAACAGTGCC |
| 7 | 361 . . . 480 | CCTACTAATCCAGCATTAAGAGAAGAGATGCGTATTCAATTCAATGACATGAACAGTGCCCCTTACAACCGCTATTCCTCTTTTGGCAGTTCAAAATTATCAAGTTCCTCTTTTATCAGTA |
| 8 | 421 . . . 540 | CTTACAACCGCTATTCCTCTTTTGGCAGTTCAAAATTATCAAGTTCCTCTTTTATCAGTATATGTTCAAGCTGCAAATTTACATTTATCAGTTTTGAGAGATGTTTCAGTGTTTGGACAA |
| 9 | 481 . . . 600 | TATGTTCAAGCTGCAAATTTACATTTATCAGTTTTGAGAGATGTTTCAGTGTTTGGACAAAGGTGGGGATTTGATGCCGCGACTATCAATAGTCGTTATAATGATTTAACTAGGCTTATT |
| 10 | 541 . . . 660 | AGGTGGGGATTTGATGCCGCGACTATCAATAGTCGTTATAATGATTTAACTAGGCTTATTGGCAACTATACAGATTATGCTGTGCGCTGGTACAATACGGGATTAGAGCGTGTATGGGA |
| 11 | 601 . . . 720 | GGCAACTATACAGATTATGCTGTGCGCTGGTACAATACGGGATTAGAGCGTGTATGGGACCGGATTCTAGAGATTGGGTAAGGTATAATCAATTTAGAAGAGAGCTAACACTTACTGTA |
| 12 | 661 . . . 780 | CCGGATTCTAGAGATTGGGTAAGGTATAATCAATTTAGAAGAGAGCTAACACTTACTGTATATTAGATATCGTTGCTCTATTCTCAAATTATGATAGTCGAAGGTATCCAATTCGAACAGTT |
| 13 | 721 . . . 840 | TTAGATATCGTTGCTCTATTCTCAAATTATGATAGTCGAAGGTATCCAATTCGAACAGTTTCCCAATTAACAAGAGAAATTTATACGAACCCAGTATTAGAAAATTTTGATGGTAGTTTT |

TABLE 5-continued

Example baits designed against Cry1Aa1.

| SEQ ID NO | Base pair range | Sequence |
|---|---|---|
| 14 | 781 . . . 900 | TCCCAATTAACAAGAGAAATTTATACGAACCCAGTATTAGAAA<br>ATTTTGATGGTAGTTTTCGTGGAATGGCTCAGAGAATAGAACA<br>GAATATTAGGCAACCACATCTTATGGATATCCTT |
| 15 | 841 . . . 960 | CGTGGAATGGCTCAGAGAATAGAACAGAATATTAGGCAACCA<br>CATCTTATGGATATCCTTAATAGTATAACCATTTATACTGAT<br>GTGCATAGAGGCTTTAATTATTGGTCAGGGCATCAA |
| 16 | 901 . . . 1020 | AATAGTATAACCATTTATACTGATGTGCATAGAGGCTTTAATT<br>ATTGGTCAGGGCATCAAATAACAGCTTCTCCTGTAGGGTTTTC<br>AGGACCAGAATTCGCATTCCCTTTATTTGGGAAT |
| 17 | 961 . . . 1080 | ATAACAGCTTCTCCTGTAGGGTTTTCAGGACCAGAATTCGCAT<br>TCCCTTTATTTGGGAATGCGGGGAATGCAGCTCCACCCGTACT<br>TGTCTCATTAACTGGTTTGGGGATTTTTAGAACA |
| 18 | 1021 . . . 1140 | GCGGGGAATGCAGCTCCACCCGTACTTGTCTCATTAACTGGTTT<br>GGGGATTTTTAGAACATTATCTTCACCTTTATATAGAAGAATTA<br>TACTTGGTTCAGGCCCAAATAATCAGGAACTG |
| 19 | 1081 . . . 1200 | TTATCTTCACCTTTATATAGAAGAATTATACTTGGTTCAGGCCC<br>AAATAATCAGGAACTGTTTGTCCTTGATGGAACGGAGTTTTCT<br>TTTGCCTCCCTAACGACCAACTTGCCTTCCACT |
| 20 | 1141 . . . 1260 | TTTGTCCTTGATGGAACGGAGTTTTCTTTTGCCTCCCTAACGA<br>CCAACTTGCCTTCCACTATATATAGACAAAGGGGTACAGTCG<br>ATTCACTAGATGTAATACCGCCACAGGATAATAGT |
| 21 | 1201 . . . 1320 | ATATATAGACAAAGGGGTACAGTCGATTCACTAGATGTAATAC<br>CGCCACAGGATAATAGTGTACCACCTCGTGCGGGATTTAGCCA<br>TCGATTGAGTCATGTTACAATGCTGAGCCAAGCA |
| 22 | 1261 . . . 1380 | GTACCACCTCGTGCGGGATTTAGCCATCGATTGAGTCATGTTA<br>CAATGCTGAGCCAAGCAGCTGGAGCAGTTTACACCTTGAGAG<br>CTCCAACGTTTTCTTGGCAGCATCGCAGTGCTGAA |

New gene discovery: To assess the capacity of this approach for new gene discovery, DNA from a strain containing Cry26 is spiked into capture reactions, and baits for Cry26 are omitted from the bait pool. Additionally, any bait derived from a homologous gene (Cry28, for example) that had greater than 80% identity to Cry26 over 60 or more bases is also excluded from the bait pool. Thus successful capture of Cry26 validates this method as an approach for discovery of "new" genes.

Gene capture reactions: 3 µg of DNA is used as starting material for the procedure. DNA shearing, capture, post-capture washing and gene amplification are performed in accordance with Agilent SureSelect® specifications. Throughout the procedure, DNA is purified with the Agencourt AMPure® XP beads, and DNA quality is evaluated with the Agilent TapeStation®. Briefly, DNA is sheared to an approximate length of 800 by using a Covaris Focused-ultrasonicator. The Agilent SureSelect® Library Prep Kit is used to repair ends, add A bases, ligate the paired-end adaptor and amplify the adaptor-ligated fragments. Prepped DNA samples are lyophillized to contain 750 ng in 3.4 µL and mixed with Agilent SureSelect® Hybridization buffers, Capture Library Mix and Block Mix. Hybridization is performed for at least 16 hours at 65° C. DNAs hybridized to biotinylated baits are precipitated with Dynabeads™ MyOne™ Streptavidin T1 magnetic beads and washed with SureSelect® Binding and Wash Buffers. Captured DNAs are PCR-amplified to add index tags and pooled for multiplexed sequencing.

Genomic DNA libraries can be generated by adding a predetermined amount of sample DNA to, for example, the Paired End Sample prep kit PE-102-1001 (ILLUMINA, Inc.) following manufacturer's protocol. Briefly, DNA fragments are generated by random shearing and conjugated to a pair of oligonucleotides in a forked adaptor configuration. The ligated products are amplified using two oligonucleotide primers, resulting in double-stranded blunt-ended products having a different adaptor sequence on either end. The libraries once generated are applied to a flowcell for cluster generation.

Clusters are formed prior to sequencing using the TruSeq PE v3 cluster kit (ILLUMINA, Inc.) following manufacturer's instructions. Briefly, products from a DNA library preparation are denatured and single strands annealed to complementary oligonucleotides on the flow-cell surface. A new strand is copied from the original strand in an extension reaction and the original strand is removed by denaturation. The adaptor sequence of the copied strand is annealed to a surface-bound complementary oligonucleotide, forming a bridge and generating a new site for synthesis of a second strand. Multiple cycles of annealing, extension and denaturation in isothermal conditions resulted in growth of clusters, each approximately 1 pm in physical diameter.

The DNA in each cluster is linearized by cleavage within one adaptor sequence and denatured, generating single-stranded template for sequencing by synthesis (SBS) to obtain a sequence read. To perform paired-read sequencing, the products of read 1 can be removed by denaturation, the template is used to generate a bridge, the second strand is re-synthesized and the opposite strand is cleaved to provide the template for the second read. Sequencing can be performed using the ILLUMINA, Inc. V4 SBS kit with 100 base paired end reads on the HiSeq® 2000. Briefly, DNA templates can be sequenced by repeated cycles of polymerase-directed single base extension. To ensure base-by-base nucleotide incorporation in a stepwise manner, a set of four reversible terminators, A, C, G and T each labeled with a different removable fluorophore are used. The use of modified nucleotides allows incorporation to be driven essentially to completion without risk of over-incorporation. It also enables addition of all four nucleotides simultaneously minimizing risk of misincorporation. After each cycle of incorporation, the identity of the inserted base is determined by laser-induced excitation of the fluorophores and fluorescence imaging is recorded. The fluorescent dye and linker is removed to regenerate an available group ready for the next cycle of nucleotide addition. The HiSeq® sequencing instrument is designed to perform multiple cycles of sequencing chemistry and imaging to collect sequence data automatically from each cluster on the surface of each lane of an eight-lane flow cell.

Bioinformatics: Sequences are assembled using the CLCBio suite of bioinformatics tools. The presence of genes of interest (Table 4) is determined by BLAST query against a database of those genes of interest. Diversity of organisms present in the sample is evaluated from 16s identifications. Process QC is evaluated based on retrieval of positive control sequences that are included in the reactions. To assess the capacity of this approach for new gene discovery, DNA from a strain containing Cry26 is spiked into capture reactions, and baits for Cry26 are omitted from the bait pool. Due to sequence homology among Cry gene family members, baits designed against a different gene (Cry28Aa) would have had greater than 80% similarity to the homologous Cry26 region. However, those baits are also excluded.

Results from sequencing captured DNA: Composition of the microbial communities in each environmental sample is analyzed indicating the number of positive control genes detected; the number of times positive control genes are detected; the number of known genes detected; and the number of new homologs (new gene sequences) are detected.

What is claimed is:

1. A method for identifying a variant of a gene of interest having less than 95% identity to said gene of interest, in a complex sample, said method comprising:
   a) preparing DNA from a complex sample comprising a variant of a gene of interest for hybridization thereby forming a prepared sample DNA, the prepared sample DNA comprising said variant of said gene of interest, wherein said gene of interest comprises a plant pest resistance gene of interest, a plant disease resistance gene of interest, and/or a herbicide tolerance gene of interest;
   b) mixing said prepared sample DNA with a labeled bait pool comprising polynucleotide sequences complementary to said plant pest resistance gene of interest, plant disease resistance gene of interest, and/or herbicide tolerance gene of interest;
   c) hybridizing the prepared sample DNA to said labeled bait pool under conditions that allow for hybridization of a labeled bait in said labeled bait pool with said variant of said plant pest resistance gene of interest, plant disease resistance gene of interest, and/or herbicide tolerance gene of interest to form one or more hybridization complexes, wherein said variant of said plant pest resistance gene of interest, plant disease resistance gene of interest, and/or herbicide tolerance gene of interest in the hybridization complexes comprises captured DNA;
   d) sequencing said captured DNA to determine a sequence read of said variant of said plant pest resistance gene of interest, plant disease resistance gene of interest, and/or herbicide tolerance gene of interest; and
   e) aligning said sequence read to a database of known sequences using a sequence alignment program in order to identify said variant of said plant pest resistance gene of interest, plant disease resistance gene of interest, and/or herbicide tolerance gene of interest having less than 95% identity to said plant pest resistance gene of interest, plant disease resistance gene of interest, and/or herbicide tolerance gene of interest.

2. The method of claim 1, wherein said complex sample is an environmental sample.

3. The method of claim 1, wherein said complex sample is a mixed culture of at least two organisms.

4. The method of claim 1, wherein said complex sample is a mixed culture of more than two organisms collected from a petri plate.

5. The method of claim 1, wherein said labeled bait pools comprise labeled baits specific for at least 500 plant pest resistance genes of interest, plant disease resistance genes of interest, and/or herbicide tolerance genes of interest.

6. The method of claim 1, wherein said labeled bait pool comprises at least 50 distinct labeled baits that are mixed with said prepared sample DNA.

7. The method of claim 1, wherein said labeled bait pool comprises labeled baits that are 50-200 nt in length.

8. The method of claim 1, wherein said labeled baits are labeled with biotin, a hapten, or an affinity tag.

9. The method of claim 1, wherein said labeled baits comprise overlapping labeled baits, said overlapping labeled baits comprising at least two labeled baits that are complementary to a portion of a plant pest resistance gene of interest, a plant disease resistance gene of interest, and/or a herbicide tolerance gene of interest, wherein the at least two labeled baits comprise different DNA sequences that are partially overlapping.

10. The method of claim 9, wherein at least 10, at least 30, at least 60, at least 90, or at least 120 nucleotides of each overlapping bait overlap with at least one other overlapping bait.

11. The method of claim 9, wherein said labeled baits cover each plant pest resistance gene of interest, plant disease resistance gene of interest, and/or herbicide tolerance gene of interest by at least 2×.

12. The method of claim 1, wherein said variant is a homolog of said plant pest resistance gene of interest, plant disease resistance gene of interest, and/or herbicide tolerance gene of interest.

13. The method of claim 1, wherein said prepared sample DNA is enriched prior to mixing with said labeled baits.

14. The method of claim 1, wherein said labeled baits are designed to target 16S DNA.

15. The method of claim 1, wherein said hybridization complex is captured and purified from unbound prepared sample DNA.

16. The method of claim 15, wherein said hybridization complex is captured using a streptavidin molecule attached to a solid phase.

17. The method of claim 16, wherein said solid phase is a magnetic bead.

18. The method of claim 1, wherein steps a), b), and c) are performed using an enrichment kit for multiplex sequencing.

19. The method of claim 1, wherein said captured DNA from said hybridization complex is amplified and index tagged prior to said sequencing.

20. The method of claim 1, wherein said sequencing comprises multiplex sequencing with gene fragments from different environmental samples.

21. The method of claim 1, wherein said labeled bait pool comprises labeled baits that are 70-150 nt in length.

22. The method of claim 1, wherein said labeled bait pool comprises labeled baits that are 100-140 nt in length.

23. The method of claim 1, wherein said labeled bait pool comprises labeled baits that are 110-130 nt in length.

* * * * *